US012667685B2

(12) United States Patent
Nortman et al.

(10) Patent No.: US 12,667,685 B2
(45) Date of Patent: Jun. 30, 2026

(54) ROBOTIC VENTILATION SYSTEM FOR CORRECT MASK PLACEMENT

(71) Applicant: Restful Robotics, Inc., Sunrise, FL (US)

(72) Inventors: Scott Nortman, Sunrise, FL (US); David Jassir, Davie, FL (US)

(73) Assignee: Restful Robotics Inc., Sunrise, FL (US)

( * ) Notice: Subject to any disclaimer, the term of this patent is extended or adjusted under 35 U.S.C. 154(b) by 1095 days.

(21) Appl. No.: 17/734,656

(22) Filed: May 2, 2022

(65) Prior Publication Data

US 2022/0257892 A1 Aug. 18, 2022

Related U.S. Application Data

(63) Continuation-in-part of application No. PCT/US2020/059803, filed on Nov. 10, 2020.

(Continued)

(51) Int. Cl.
*A61M 16/06* (2006.01)
*A61B 34/32* (2016.01)
(Continued)

(52) U.S. Cl.
CPC ............. *A61M 16/06* (2013.01); *A61B 34/32* (2016.02); *A61M 16/022* (2017.08); *A61M 16/024* (2017.08); *A61M 16/0616* (2014.02); *A61M 16/0683* (2013.01); *A61M 16/0875* (2013.01); *A61B 2034/2065* (2016.02); *A61M 2205/0216* (2013.01); *A61M 2205/13* (2013.01); *A61M 2205/3303* (2013.01); *A61M 2205/587* (2013.01); *A61M 2209/082* (2013.01); *A61M 2210/0618* (2013.01); *A61M 2210/0625* (2013.01); *A61M 2230/04* (2013.01);

(Continued)

(58) Field of Classification Search
CPC .............. A61M 16/06; A61M 16/0683; A61M 2210/0618; A61M 2210/0625; A61M 2230/18; A61M 2205/13; A61B 34/32; A61B 34/30; A61B 2034/2065
See application file for complete search history.

(56) References Cited

U.S. PATENT DOCUMENTS

| | | | | |
|---|---|---|---|---|
| 2014/0039517 A1* | 2/2014 | Bowling | ................ | A61B 34/74 |
| | | | | 606/130 |
| 2017/0245946 A1* | 8/2017 | Tabandeh | ................ | A61B 34/20 |
| 2018/0220897 A1* | 8/2018 | Meger | .................... | G01G 19/44 |

FOREIGN PATENT DOCUMENTS

CN 108969858 A * 12/2018 ........ A61M 16/0051

* cited by examiner

*Primary Examiner* — Brandy S Lee
*Assistant Examiner* — Rohan Patel
(74) *Attorney, Agent, or Firm* — J. Steven Svoboda

(57) ABSTRACT

A system includes: a robot comprising an arm, the arm comprising a flange, the flange coupled to an end of the arm, the arm configured to move the flange along a degree of freedom; a mask coupled to the flange, the mask configured to deliver gas to a user, wherein the arm further comprises a kinematic mount, the kinematic mount usable to do one or more of orient and locate the mask with respect to the flange; a ventilator coupled to the mask, the ventilator configured to deliver the gas to the mask; a gas tube coupled to both the mask and the ventilator, the gas tube configured to carry gas between the ventilator and the mask; and a tracking system, the tracking system configured to capture image data of one or more of the mask and a face of the user.

30 Claims, 9 Drawing Sheets

Related U.S. Application Data

(60) Provisional application No. 62/933,620, filed on Nov. 11, 2019.

(51) Int. Cl.
*A61M 16/00* (2006.01)
*A61M 16/08* (2006.01)
*A61B 34/20* (2016.01)

(52) U.S. Cl.
CPC ..... *A61M 2230/18* (2013.01); *A61M 2230/42* (2013.01); *A61M 2230/50* (2013.01); *A61M 2230/63* (2013.01)

FIG. 5

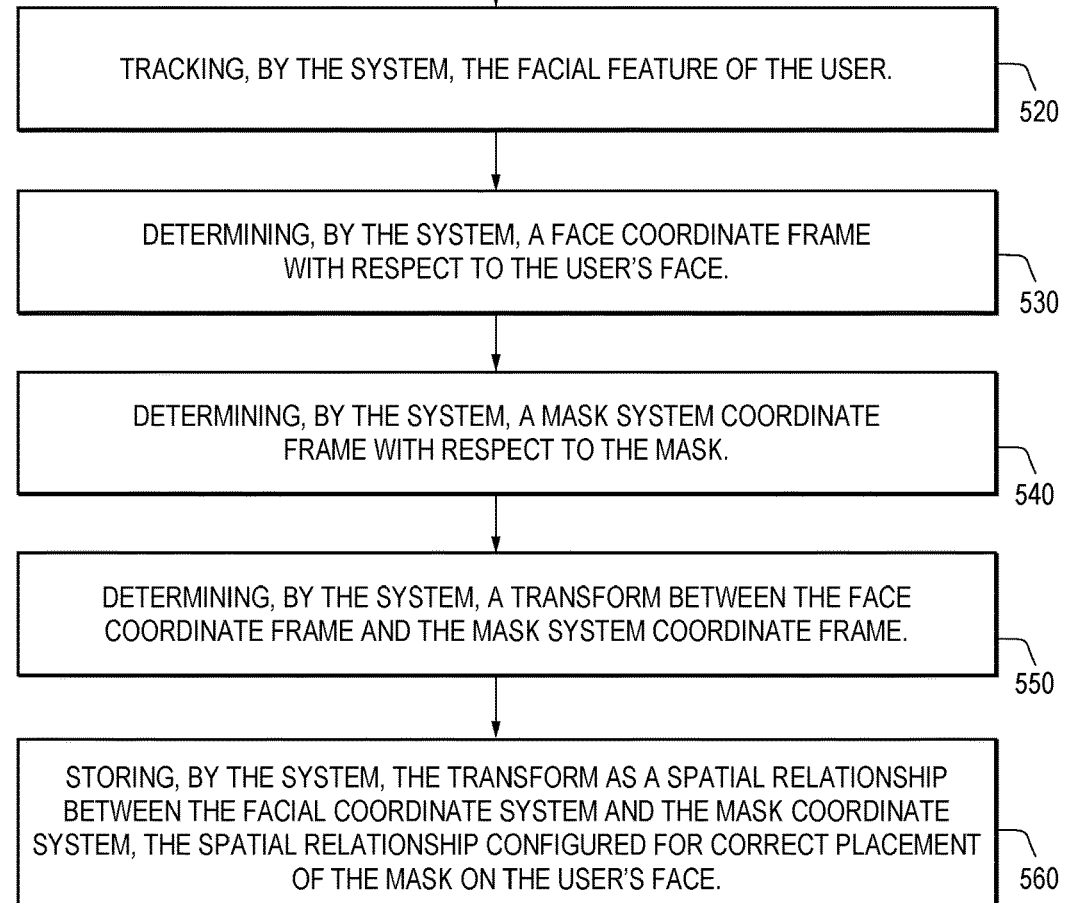

IMAGE DATA IS CAPTURED, THE IMAGE DATA COMPRISING A FACIAL FEATURE OF A USER, BY A SYSTEM COMPRISING: A ROBOT COMPRISING AN ARM, THE ARM COMPRISING A FLANGE, THE FLANGE COUPLED TO AN END OF THE ARM, THE ARM CONFIGURED TO MOVE THE FLANGE ALONG A DEGREE OF FREEDOM; A MASK COUPLED TO THE FLANGE, THE MASK CONFIGURED TO DELIVER GAS TO A USER, WHEREIN THE ARM FURTHER COMPRISES A KINEMATIC MOUNT, THE KINEMATIC MOUNT USABLE TO DO ONE OR MORE OF ORIENT AND LOCATE THE MASK WITH RESPECT TO THE FLANGE; A VENTILATOR COUPLED TO THE MASK, THE VENTILATOR CONFIGURED TO DELIVER THE GAS TO THE MASK; A GAS TUBE COUPLED TO BOTH THE MASK AND THE VENTILATOR, THE GAS TUBE CONFIGURED TO CARRY GAS BETWEEN THE VENTILATOR AND THE MASK; A CONTROLLER CONFIGURED TO CHANGE A POSE OF THE MASK, THE CONTROLLER FURTHER CONFIGURED TO CONTROL THE DELIVERY OF THE GAS FROM THE VENTILATOR TO THE USER; AND A TRACKING SYSTEM, THE TRACKING SYSTEM CONFIGURED TO CAPTURE IMAGE DATA OF ONE OR MORE OF THE MASK AND A FACE OF THE USER, WHEREIN THE CONTROLLER IS CONFIGURED TO CHANGE THE MASK POSE BASED AT LEAST IN PART ON THE IMAGE DATA. FOR EXAMPLE, THE TRACKING SYSTEM CAPTURES THE IMAGE DATA, THE IMAGE DATA COMPRISING THE FACIAL FEATURE OF THE USER. OPTIONALLY, THE IMAGE DATA FURTHER COMPRISES IMAGE DATA REGARDING THE FIDUCIAL MARKER. OPTIONALLY, THE IMAGE DATA FURTHER COMPRISES IMAGE DATA REGARDING A FACIAL FIDUCIAL MARKER COMPRISED IN THE USER'S FACE.

TRACKING, BY THE SYSTEM, THE FACIAL FEATURE OF THE USER.

DETERMINING, BY THE SYSTEM, A FACE COORDINATE FRAME WITH RESPECT TO THE USER'S FACE.

DETERMINING, BY THE SYSTEM, A MASK SYSTEM COORDINATE FRAME WITH RESPECT TO THE MASK.

DETERMINING, BY THE SYSTEM, A TRANSFORM BETWEEN THE FACE COORDINATE FRAME AND THE MASK SYSTEM COORDINATE FRAME.

STORING, BY THE SYSTEM, THE TRANSFORM AS A SPATIAL RELATIONSHIP BETWEEN THE FACIAL COORDINATE SYSTEM AND THE MASK COORDINATE SYSTEM, THE SPATIAL RELATIONSHIP CONFIGURED FOR CORRECT PLACEMENT OF THE MASK ON THE USER'S FACE.

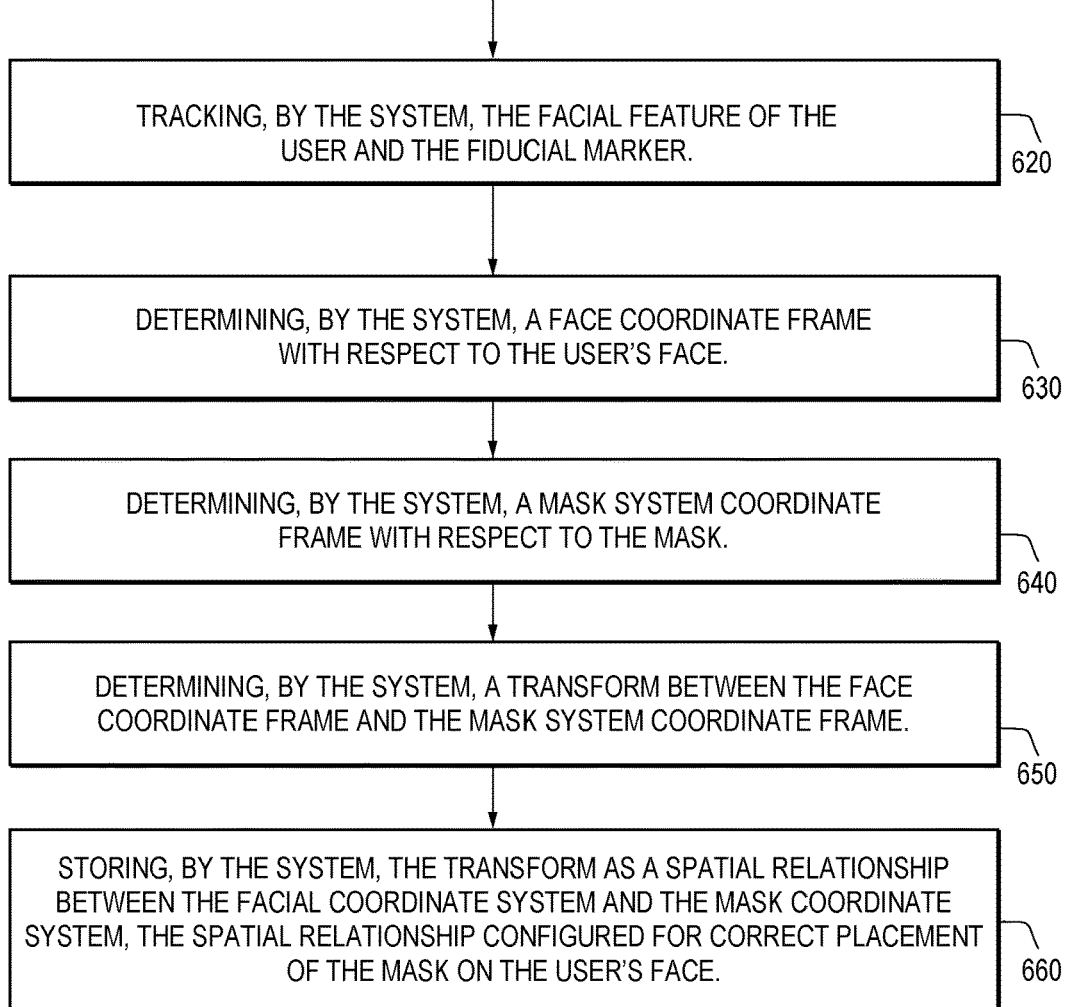

IMAGE DATA IS CAPTURED, THE IMAGE DATA COMPRISING A FACIAL FEATURE OF A USER, THE IMAGE DATA FURTHER COMPRISING IMAGE DATA REGARDING THE FIDUCIAL MARKER, BY A SYSTEM COMPRISING: A ROBOT COMPRISING AN ARM, THE ARM COMPRISING A FLANGE, THE FLANGE COUPLED TO AN END OF THE ARM, THE ARM CONFIGURED TO MOVE THE FLANGE ALONG A DEGREE OF FREEDOM; A MASK COUPLED TO THE FLANGE, THE MASK CONFIGURED TO DELIVER GAS TO A USER, THE MASK COMPRISING A FIDUCIAL MARKER; A VENTILATOR COUPLED TO THE MASK, THE VENTILATOR CONFIGURED TO DELIVER THE GAS TO THE MASK; A GAS TUBE COUPLED TO BOTH THE MASK AND THE VENTILATOR, THE GAS TUBE CONFIGURED TO CARRY THE GAS BETWEEN THE VENTILATOR AND THE MASK; A CONTROLLER CONFIGURED TO CHANGE A POSE OF THE MASK, THE CONTROLLER FURTHER CONFIGURED TO CONTROL THE DELIVERY OF THE GAS FROM THE VENTILATOR TO THE USER; AND A TRACKING SYSTEM, THE TRACKING SYSTEM CONFIGURED TO CAPTURE IMAGE DATA OF ONE OR MORE OF THE MASK AND A FACE OF THE USER, THE TRACKING SYSTEM FURTHER CONFIGURED TO TRACK THE FIDUCIAL MARKER, WHEREIN THE CONTROLLER IS CONFIGURED TO CHANGE THE MASK POSE BASED AT LEAST IN PART ON THE IMAGE DATA.

TRACKING, BY THE SYSTEM, THE FACIAL FEATURE OF THE USER AND THE FIDUCIAL MARKER.

620

DETERMINING, BY THE SYSTEM, A FACE COORDINATE FRAME WITH RESPECT TO THE USER'S FACE.

630

DETERMINING, BY THE SYSTEM, A MASK SYSTEM COORDINATE FRAME WITH RESPECT TO THE MASK.

640

DETERMINING, BY THE SYSTEM, A TRANSFORM BETWEEN THE FACE COORDINATE FRAME AND THE MASK SYSTEM COORDINATE FRAME.

650

STORING, BY THE SYSTEM, THE TRANSFORM AS A SPATIAL RELATIONSHIP BETWEEN THE FACIAL COORDINATE SYSTEM AND THE MASK COORDINATE SYSTEM, THE SPATIAL RELATIONSHIP CONFIGURED FOR CORRECT PLACEMENT OF THE MASK ON THE USER'S FACE.

IMAGE DATA IS CAPTURED, THE IMAGE DATA COMPRISING A FACIAL FEATURE OF A USER, BY A SYSTEM COMPRISING: A ROBOT COMPRISING AN ARM, THE ARM COMPRISING A FLANGE, THE FLANGE COUPLED TO AN END OF THE ARM, THE ARM CONFIGURED TO MOVE THE FLANGE ALONG A DEGREE OF FREEDOM, THE ARM FURTHER COMPRISING A KINEMATIC MOUNT; A MASK COUPLED TO THE FLANGE BY A MOUNTING FEATURE CONFIGURED FOR INTERMITTENT ATTACHMENT, THE MASK CONFIGURED TO DELIVER GAS TO A USER, WHEREIN THE KINEMATIC MOUNT IS USABLE TO DO ONE OR MORE OF ORIENT AND LOCATE THE MASK WITH RESPECT TO THE FLANGE; A MASK COUPLED TO THE ROBOT, WHEREIN THE MASK IS COUPLED TO THE FLANGE BY A MOUNTING FEATURE CONFIGURED FOR INTERMITTENT ATTACHMENT, THE MOUNTING FEATURE COMPRISING THE KINEMATIC MOUNT, THE MOUNTING FEATURE FURTHER COMPRISING AN OPENING, WHEREIN THE MOUNTING FEATURE FURTHER COMPRISES A SENSOR, THE SENSOR CONFIGURED TO VERIFY THAT PROPER SEATING HAS OCCURRED OF THE MASK ON THE USER, WHEREIN A SPATIAL ALIGNMENT OF THE MASK WITH RESPECT TO THE KINEMATIC MOUNT IS KNOWN A PRIORI, WHEREIN THE MASK FURTHER COMPRISES A FIDUCIAL MARKER, THE FIDUCIAL MARKER CONFIGURED TO BE TRACKED BY A TRACKING SYSTEM; A VENTILATOR COUPLED TO THE MASK, THE VENTILATOR CONFIGURED TO DELIVER THE GAS TO THE MASK, WHEREIN THE GAS PASSES THROUGH THE OPENING, WHEREIN THE OPENING COMPRISES A SENSOR, THE SENSOR CONFIGURED TO DETECT THE GAS; A GAS TUBE COUPLED TO BOTH THE MASK AND THE VENTILATOR, THE GAS TUBE CONFIGURED TO CARRY THE GAS BETWEEN THE VENTILATOR AND THE MASK; A CONTROLLER CONFIGURED TO CHANGE A POSE OF THE MASK, THE CONTROLLER FURTHER CONFIGURED TO CONTROL THE DELIVERY OF THE GAS FROM THE VENTILATOR TO THE USER, WHEREIN FOLLOWING A START OF DELIVERY OF PRESSURIZED GAS TO THE USER, THE CONTROLLER COMMANDS THE ARM TO MAINTAIN BOTH AN APPROPRIATE CONTACT FORCE WITH RESPECT TO THE USER'S FACE AND AN APPROPRIATE POSITION WITH RESPECT TO THE USER'S FACE, WHEREIN THE APPROPRIATE CONTACT FORCE AND THE APPROPRIATE POSITION CREATE A SAFE AND EFFECTIVE CONTACT ENGAGEMENT BETWEEN THE MASK AND THE FACE OF THE USER, WHEREIN FOLLOWING A FAILURE OF THE SYSTEM TO MAINTAIN THE ARM AT BOTH AN APPROPRIATE CONTACT FORCE AND AN APPROPRIATE POSITION, THE SYSTEM IS CONFIGURED TO RETRACT THE ARM SO AS TO MOVE THE MASK AWAY FROM THE FACE OF THE USER, WHEREIN THE SYSTEM IS FURTHER CONFIGURED, FOLLOWING RETRACTION OF THE ARM, TO GO INTO A MODE IN WHICH THE SYSTEM AWAITS ENTRY BY THE USER INTO A REQUISITE SLEEP STATE, WHEREIN UPON ENTRY BY THE USER INTO THE REQUISITE SLEEP STATE, THE SYSTEM MOVES THE ARM TOWARD THE FACE OF THE USER; A TRACKING SYSTEM, THE TRACKING SYSTEM CONFIGURED TO CAPTURE IMAGE DATA OF ONE OR MORE OF THE MASK AND A FACE OF THE USER, THE TRACKING SYSTEM CONFIGURED TO IDENTIFY A FACE FEATURE POINT, WHEREIN THE FACE FEATURE POINT COMPRISES ONE OR MORE OF AN EYE CENTER POINT, A NOSE CENTER POINT, A MOUTH LATERAL POINT, AND A MOUTH CENTER POINT, WHEREIN THE SYSTEM MOVES THE ARM TOWARD THE FACE OF THE USER AFTER THE FACE FEATURE POINT IS IDENTIFIED, WHEREIN THE CONTROLLER IS CONFIGURED TO CHANGE THE MASK POSE BASED ON ONE OR MORE OF THE IMAGE DATA, LAPSE OF A PREDETERMINED PERIOD OF TIME, AND AN ESTIMATED SLEEP STATE OF THE USER, WHEREIN THE PREDETERMINED PERIOD OF TIME REPRESENTS AN INDICATION BY THE USER TO THE SYSTEM THAT THE USER IS GOING TO SLEEP AFTER THE PREDETERMINED PERIOD OF TIME, WHEREIN THE ESTIMATED SLEEP STATE COMPRISES ONE OR MORE OF A REQUISITE SLEEP STATE AND AN ESTIMATION OF STABILITY OF THE USER'S SLEEP STATE, WHEREIN THE SYSTEM PLACES THE MASK ON THE FACE OF THE USER AFTER THE PREDETERMINED PERIOD OF TIME HAS LAPSED, THE ROBOT COMPRISING THE TRACKING SYSTEM; AND A BIOMETRIC SENSOR SYSTEM, THE BIOMETRIC SENSOR SYSTEM COMPRISING A BIOMETRIC SENSOR, WHEREIN THE CONTROLLER IS FURTHER CONFIGURED TO CHANGE THE POSE OF THE MASK BASED AT LEAST IN PART ON BIOMETRIC DATA FROM THE BIOMETRIC SENSOR SYSTEM.

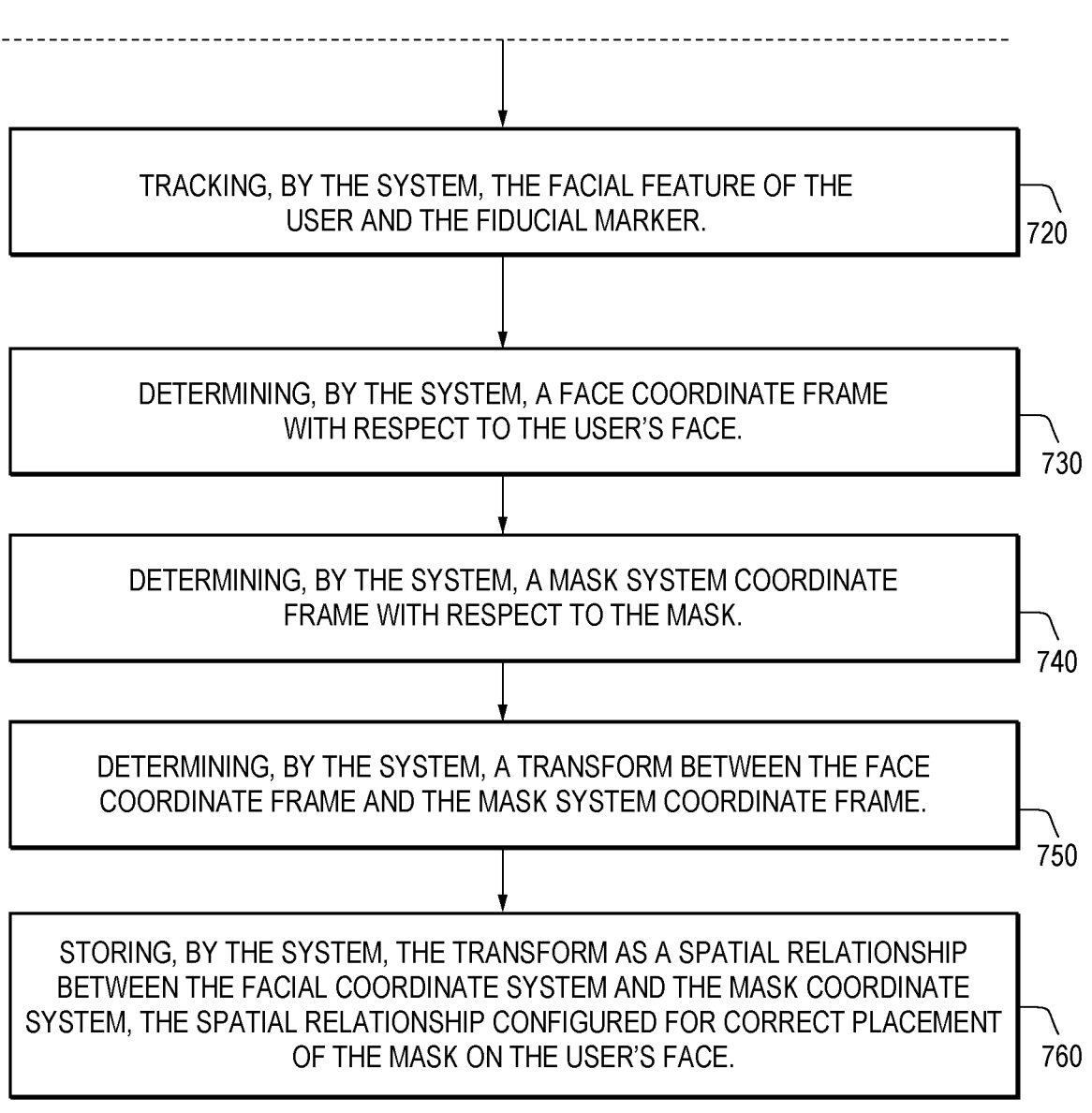

TRACKING, BY THE SYSTEM, THE FACIAL FEATURE OF THE
USER AND THE FIDUCIAL MARKER.                                720

DETERMINING, BY THE SYSTEM, A FACE COORDINATE FRAME
WITH RESPECT TO THE USER'S FACE.                             730

DETERMINING, BY THE SYSTEM, A MASK SYSTEM COORDINATE
FRAME WITH RESPECT TO THE MASK.                              740

DETERMINING, BY THE SYSTEM, A TRANSFORM BETWEEN THE FACE
COORDINATE FRAME AND THE MASK SYSTEM COORDINATE FRAME.      750

STORING, BY THE SYSTEM, THE TRANSFORM AS A SPATIAL RELATIONSHIP
BETWEEN THE FACIAL COORDINATE SYSTEM AND THE MASK COORDINATE
SYSTEM, THE SPATIAL RELATIONSHIP CONFIGURED FOR CORRECT PLACEMENT
OF THE MASK ON THE USER'S FACE.                              760

ROBOTIC VENTILATION SYSTEM FOR CORRECT MASK PLACEMENT

PRIORITY CLAIM

The present application is a continuation-in-part that claims the priority benefit of Patent Cooperation Treaty application number PCT/US2020/059803, filed Nov. 10, 2020 and entitled, "Automatic Placement of a Mask," which in turn claims priority from U.S. provisional patent application No. 62/933,620 filed Nov. 11, 2019 and entitled "Apparatus and Method for Automatic Placement of a CPAP Mask."

CROSS-REFERENCE TO RELATED APPLICATION

This application contains subject matter that is related to the subject matter of the following applications, which are assigned to the same assignee as this application. The below-listed application is hereby incorporated herein by reference in its entirety:

"ROBOTIC VENTILATION METHOD CONFIGURED FOR AUTOMATIC GAS DELIVERY," by Nortman, et al., co-filed herewith.

FIELD OF THE INVENTION

The present disclosure relates to medical systems, devices, and methods, and more specifically to a robotic ventilation system, and still more specifically to a robotic ventilation system comprising a kinematic mount and a fiducial marker.

BRIEF DESCRIPTION OF THE DRAWINGS

FIG. 5 is a flow chart of a method for correct mask placement using a robotic ventilation system including a kinematic mount.

FIG. 6 is a flow chart of a method for correct mask placement using a robotic ventilation system including a fiducial marker.

FIG. 7 is a flow chart of a method for correct mask placement using a robotic ventilation system including a kinematic mount and further including a fiducial marker.

Figure 1A:
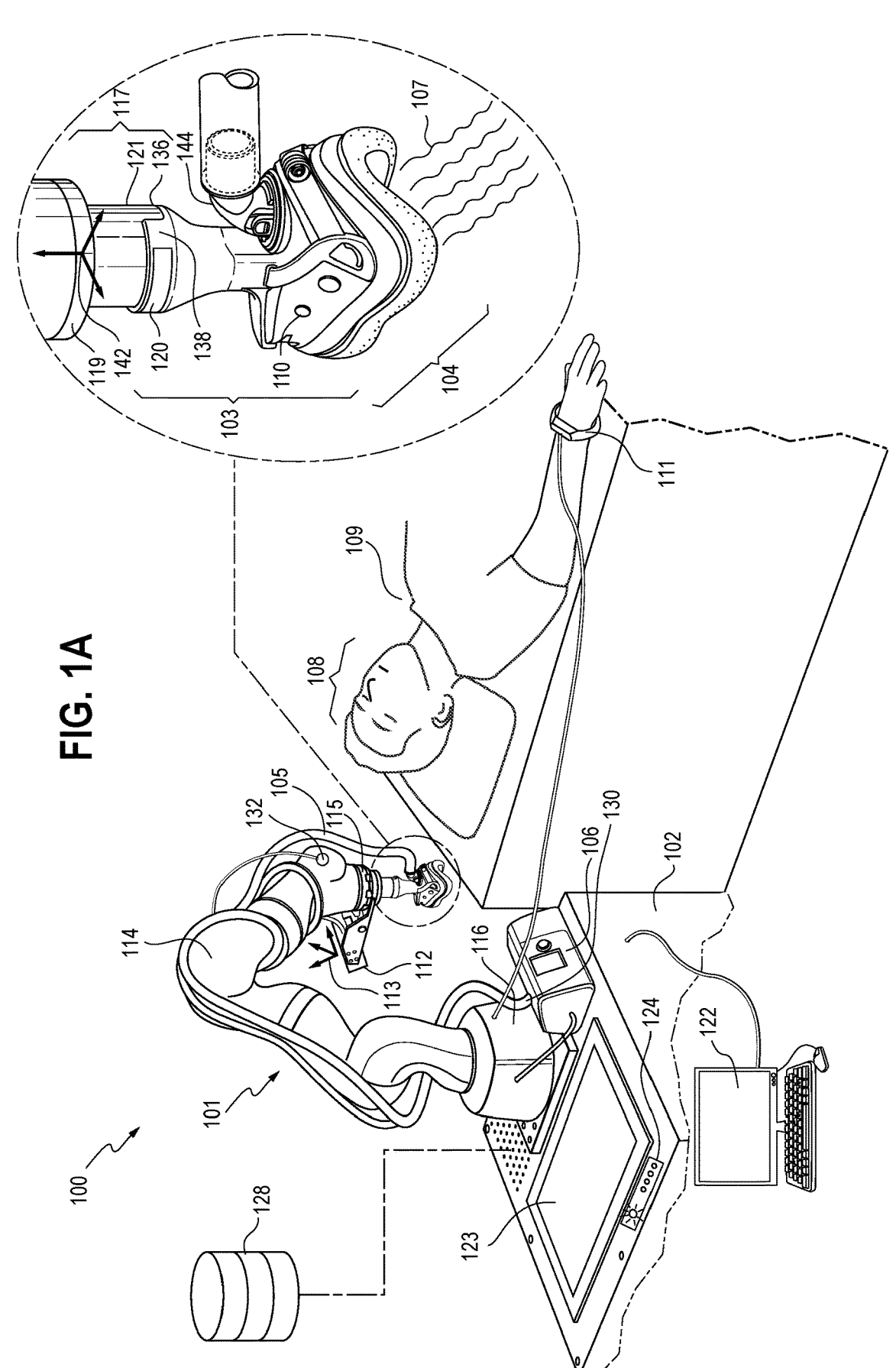
FIG. 1A is a drawing of a robotic ventilation system.

The figures depict various embodiments for purposes of illustration only. One skilled in the art will readily recognize from the following discussion that alternative embodiments of the structure and methods illustrated herein may be employed without departing from the principles described herein.

SUMMARY

A robotic ventilation system for correct mask placement comprising a kinematic mount includes: a robot comprising an arm, the arm comprising a flange, the flange coupled to an end of the arm, the arm configured to move the flange along a degree of freedom; a mask coupled to the flange, the mask configured to deliver gas to a user, wherein the arm further comprises a kinematic mount, the kinematic mount usable to do one or more of orient and locate the mask with respect to the flange; a ventilator coupled to the mask, the ventilator configured to deliver the gas to the mask; a gas tube coupled to both the mask and the ventilator, the gas tube configured to carry gas between the ventilator and the mask; a controller configured to change a pose of the mask, the controller further configured to control the delivery of the gas from the ventilator to the user; and a tracking system, the tracking system configured to capture image data of one or more of the mask and a face of the user, wherein the controller is configured to change the mask pose based at least in part on the image data.

A robotic ventilation system for correct mask placement comprising a fiducial marker includes: a robot comprising an arm, the arm comprising a flange, the flange coupled to an end of the arm, the arm configured to move the flange along a degree of freedom; a mask coupled to the flange, the mask configured to deliver gas to a user, the mask comprising a fiducial marker; a ventilator coupled to the mask, the ventilator configured to deliver the gas to the mask; a gas tube coupled to both the mask and the ventilator, the gas tube configured to carry the gas between the ventilator and the mask; a controller configured to change a pose of the mask, the controller further configured to control the delivery of the gas from the ventilator to the user; and a tracking system, the tracking system configured to capture image data of one or more of the mask and a face of the user, the tracking system further configured to track the fiducial marker, wherein the controller is configured to change the mask pose based at least in part on the image data.

A robotic ventilation system for correct mask placement comprising a kinematic mount and a fiducial marker includes: a robot comprising an arm, the arm comprising a flange, the flange coupled to an end of the arm, the arm configured to move the flange along a degree of freedom, the arm further comprising a kinematic mount; a mask coupled to the flange by a mounting feature configured for intermittent attachment, the mask configured to deliver gas to a user, wherein the kinematic mount is usable to do one or more of orient and locate the mask with respect to the flange; a mask coupled to the robot, wherein the mask is coupled to the flange by a mounting feature configured for intermittent attachment, the mounting feature comprising the kinematic mount, the mounting feature further comprising an opening, wherein the mounting feature further comprises a sensor, the sensor configured to verify that proper seating has occurred of the mask on the user, wherein a spatial alignment of the mask with respect to the kinematic mount is known a priori, wherein the mask further comprises a fiducial marker, the fiducial marker configured to be tracked by a tracking system; a ventilator coupled to the mask, the ventilator configured to deliver the gas to the mask, wherein the gas passes through the opening, wherein the opening comprises a sensor, the sensor configured to detect the gas; a gas tube coupled to both the mask and the ventilator, the gas tube configured to carry the gas between the ventilator and the mask; a controller configured to change a pose of the mask, the controller further configured to control the delivery of the gas from the ventilator to the user, wherein following a start of delivery of pressurized gas to the user, the controller commands the arm to maintain both an appropriate contact force with respect to the user's face and an appropriate position with respect to the user's face, wherein the appropriate contact force and the appropriate position create a safe and effective contact engagement between the mask and the face of the user, wherein following a failure of the system to maintain the arm at both an appropriate contact force and an appropriate position, the system is configured to retract the arm so as to move the mask away from the face of the user, wherein the system is further configured, following retraction of the arm, to go into a mode in which the system awaits entry by the user into a requisite sleep state, wherein upon entry by the user into the requisite sleep state, the system moves the arm toward the face of the user; a tracking system, the tracking system configured to capture image data of one or more of the mask and a face of the user, the tracking system configured to identify a face feature point, wherein the face feature point comprises one or more of an eye center point, a nose center point, a mouth lateral point, and a mouth center point, wherein the system moves the arm toward the face of the user after the face feature point is identified, wherein the controller is configured to change the mask pose based on one or more of the image data, lapse of a predetermined period of time, and an estimated sleep state of the user, wherein the predetermined period of time represents an indication by the user to the system that the user is going to sleep after the predetermined period of time, wherein the estimated sleep state comprises one or more of a requisite sleep state and an estimation of stability of the user's sleep state, wherein the system places the mask on the face of the user after the predetermined period of time has lapsed, the robot comprising the tracking system; and a biometric sensor system, the biometric sensor system comprising a biometric sensor, wherein the controller is further configured to change the pose of the mask based at least in part on biometric data from the biometric sensor system.

A method for correct mask placement using a robotic ventilation system comprising a kinematic mount includes: capturing image data, the image data comprising a facial feature of a user, by a system including: a robot comprising an arm, the arm comprising a flange, the flange coupled to an end of the arm, the arm configured to move the flange along a degree of freedom; a mask coupled to the flange, the mask configured to deliver gas to a user, wherein the arm further comprises a kinematic mount, the kinematic mount usable to do one or more of orient and locate the mask with respect to the flange; a ventilator coupled to the mask, the ventilator configured to deliver the gas to the mask; a gas tube coupled to both the mask and the ventilator, the gas tube configured to carry gas between the ventilator and the mask; a controller configured to change a pose of the mask, the controller further configured to control the delivery of the gas from the ventilator to the user; and a tracking system, the tracking system configured to capture image data of one or more of the mask and a face of the user, wherein the controller is configured to change the mask pose based at least in part on the image data; tracking, by the system, the facial feature of the user; determining, by the system, a face coordinate frame with respect to the user's face; determining, by the system, a mask system coordinate frame with respect to the mask; determining a transform, by the system, between the face coordinate frame and the mask system coordinate frame; and storing the transform, by the system, as a spatial relationship between the facial coordinate system and the mask coordinate system, the spatial relationship configured for correct placement of the mask on the user's face.

A method for correct mask placement using a robotic ventilation system comprising a fiducial marker includes: capturing image data, the image data comprising a facial feature of a user, the image data further comprising image data regarding a fiducial marker, by a system including: a robot comprising an arm, the arm comprising a flange, the flange coupled to an end of the arm, the arm configured to move the flange along a degree of freedom; a mask coupled to the flange, the mask configured to deliver gas to a user, the mask comprising the fiducial marker; a ventilator coupled to the mask, the ventilator configured to deliver the gas to the mask; a gas tube coupled to both the mask and the ventilator, the gas tube configured to carry the gas between the ventilator and the mask; a controller configured to change a pose of the mask, the controller further configured to control the delivery of the gas from the ventilator to the user; and a tracking system, the tracking system configured to capture image data of one or more of the mask and a face of the user, the tracking system further configured to track the fiducial marker, wherein the controller is configured to change the mask pose based at least in part on the image data; tracking, by the system, the facial feature of the user; determining, by the system, a face coordinate frame with respect to the user's face; determining, by the system, a mask system coordinate frame with respect to the mask; determining a transform, by the system, between the face coordinate frame and the mask system coordinate frame; and storing the transform, by the system, as a spatial relationship between the facial coordinate system and the mask coordinate system, the spatial relationship configured for correct placement of the mask on the user's face.

A method for correct mask placement using a robotic ventilation system comprising a kinematic mount includes: capturing image data, the image data comprising a facial feature of a user, by a system including: a robot comprising an arm, the arm comprising a flange, the flange coupled to an end of the arm, the arm configured to move the flange along a degree of freedom, the arm further comprising a kinematic mount; a mask coupled to the flange by a mounting feature configured for intermittent attachment, the mask configured to deliver gas to a user, wherein the kinematic mount is usable to do one or more of orient and locate the mask with respect to the flange; a mask coupled to the robot, wherein the mask is coupled to the flange by a mounting feature configured for intermittent attachment, the mounting feature comprising the kinematic mount, the mounting feature further comprising an opening, wherein the mounting feature further comprises a sensor, the sensor configured to verify that proper seating has occurred of the mask on the user, wherein a spatial alignment of the mask with respect to the kinematic mount is known a priori, wherein the mask further comprises a fiducial marker, the fiducial marker configured to be tracked by a tracking system; a ventilator coupled to the mask, the ventilator configured to deliver the gas to the mask, wherein the gas passes through the opening, wherein the opening comprises a sensor, the sensor configured to detect the gas; a gas tube coupled to both the mask and the ventilator, the gas tube configured to carry the gas between the ventilator and the mask; a controller configured to change a pose of the mask, the controller further configured to control the delivery of the gas from the ventilator to the user, wherein following a start of delivery of pressurized gas to the user, the controller commands the arm to maintain both an appropriate contact force with respect to the user's face and an appropriate position with respect to the user's face, wherein the appropriate contact force and the appropriate position create a safe and effective contact engagement between the mask and the face of the user, wherein following a failure of the system to maintain the arm at both an appropriate contact force and an appropriate position, the system is configured to retract the arm so as to move the mask away from the face of the user, wherein the system is further configured, following retraction of the arm, to go into a mode in which the system awaits entry by the user into a requisite sleep state, wherein upon entry by the user into the requisite sleep state, the system moves the arm toward the face of the user; a tracking system, the tracking system configured to capture image data of one or more of the mask and a face of the user, the tracking system configured to identify a face feature point, wherein the face feature point comprises one or more of an eye center point, a nose center point, a mouth lateral point, and a mouth center point, wherein the system moves the arm toward the face of the user after the face feature point is identified, wherein the controller is configured to change the mask pose based on one or more of the image data, lapse of a predetermined period of time, and an estimated sleep state of the user, wherein the predetermined period of time represents an indication by the user to the system that the user is going to sleep after the predetermined period of time, wherein the estimated sleep state comprises one or more of a requisite sleep state and an estimation of stability of the user's sleep state, wherein the system places the mask on the face of the user after the predetermined period of time has lapsed, the robot comprising the tracking system; and a biometric sensor system, the biometric sensor system comprising a biometric sensor, wherein the controller is further configured to change the pose of the mask based at least in part on biometric data from the biometric sensor system; tracking, by the system, the facial feature of the user; determining, by the system, a face coordinate frame with respect to the user's face; determining, by the system, a mask system coordinate frame with respect to the mask; determining a transform, by the system, between the face coordinate frame and the mask system coordinate frame; and storing the transform, by the system, as a spatial relationship between the facial coordinate system and the mask coordinate system, the spatial relationship configured for correct placement of the mask on the user's face.

DETAILED DESCRIPTION

The disclosure describes a system and method for correct placement and for proper force application of a ventilator mask onto a face of a user, and for maintaining the proper placement and force application of the mask while the user does one or more of sleep and move.

A robotic arm has the mask operatively coupled to its distal end, and a robot base is placed beside the user. The reach and dexterity of the robotic arm can allow for correct placement and for proper force application of the mask onto the face of the user while the user does one or more of lie in bed and move during sleep.

The distal end of the robotic arm can also be operatively coupled to a computer vision system that views the face of the user and optically tracks needed facial features, in real-time, to cause the robotic arm to maintain correct alignment of the mask with the face of the user.

A biometric sensor system can measure and analyze signals of the user to determine a sleep state of the user in real-time, and can cause the robotic arm to position and orient the mask after the user has entered a specified sleep state.

FIG. 1A is a drawing of a robotic ventilation system 100. The system 100 comprises a robot 101 and a base 102 operably connected to the robot 101. The robot 101 comprises a mask system 103. The mask system 103 comprises a mask 104, the mask 104 configured to deliver the breathable gas 107 to the user 109. The mask 104 comprises one or more of a face mask, a partial face mask, a nasal mask, a mouth mask, a nasal pillow mask, and a nasal plug mask. The robot 101 further comprises a tube 105, the tube 105 operably connected to the mask system 103. The base 102 comprises a ventilator 106, the ventilator 106 configured to deliver breathable gas 107 to the mask 104 through the tube 105. The mask 104 then delivers the gas 107 to a face 108 of a user 109. Alternative embodiments comprise the ventilator 106 as a standalone ventilator 106. Alternatively, or additionally, the ventilator 106 is positioned outside of the base 102.

The system 100 is configured to deliver the breathable gas 107 to the user 109 via the mask 104. For example, the system 100 delivers the breathable gas 107 to the user 109 via the mask 104 after detecting a state of the user 109. More specifically, the system 100 delivers the breathable gas 107 to the user 109 via the mask 104 after detecting a requisite sleep state of the user 109. The requisite sleep state may be predetermined by the user 109. Alternatively, or additionally, the requisite sleep state may be determined by the system 100. For example, the requisite sleep state may be calculated by the system 100. For example, the requisite sleep state comprises one or more of a wakeful state, a stage 1 non-rapid eye movement (non-REM) sleep state, a stage 2 non-REM sleep state, a stage 3 non-REM sleep state, and an REM sleep state. Even more specifically, the system 100 delivers the breathable gas 107 to the user 109 after the user 109 falls asleep. Alternatively, or additionally, the system 100 delivers the breathable gas 107 to the user 109 after fulfillment of a time-based condition. For example, the system 100 delivers the breathable gas 107 to the user 109 after one or more of passage of a predetermined amount of time and after a predetermined time of day is reached.

Optionally, the mask 104 further comprises a fiducial marker 110. The fiducial marker 110 comprises a tracked object 110 placed at a known pose in a sensing area of a tracking system that can be viewed by the tracking system and can serve as a reference for the tracking system.

For example, the fiducial marker comprises a circular fiducial marker such as the MBA08MMA manufactured by NaturalPoint, Inc., of Corvallis, Oregon (www.naturalpoint.com). For example, the fiducial marker comprises a spherical fiducial marker such as the MKR064M3-10 manufactured by NaturalPoint, Inc., of Corvallis, Oregon (www.naturalpoint.com). For example, the fiducial marker comprises a square fiducial marker such as the ArUco developed by Universitario de Rabanales, University of Córdoba, 14071, Córdoba, Spain (www.uco.es).

The robot 102 further comprises a biometric sensor system 111, the biometric sensor system 111 configured to sense biometric information regarding the user 109. For example, the biometric information comprises one or more of a heart rate, a respiratory rate, a temperature, a blood oxygen saturation level, an eye state, motion or lack thereof, an estimated sleep state, a sleep profile, a blood pressure, a pulse rate, a temperature, an eye state, a height, a weight, an age, and other biometric information. For example, tracked facial features of the user can be observed using a non-computer-vision-based approach, such as radar, LIDAR, ultrasound, or any other suitable spatial measuring method. For example, the current sleep state is determined using a remote camera comprised in the biometric sensor system 111. For example, the biometric sensor system 111 comprises one or more of a camera and a watch.

For example, the biometric sensor system 111 is physically attached to the user 109. Alternatively, or additionally, the biometric sensor system 111 comprises a remote biometric sensor system 111 that is not physically attached to the user 109. For example, the biometric sensor system 111 is comprised in a virtual assistant device such as the Alexa device sold by Amazon.com of Seattle, Washington (www.amazon.com).

The system 100 further comprises a tracking system 112 configured to track one or more of the mask system 103, the fiducial marker 110, and a face feature point of the user 109. The tracking system is further configured to capture image data. The image data comprises a facial feature (not shown in FIG. 1A; item 407 in FIG. 4) of the user 109. For example, the tracking system 112 comprises a camera system configured to capture the image data.

While a computer vision system 112 is a preferred implementation of the invention, more broadly, any tracking system 112 will work, including one or more of a computer vision system, a radio detection and ranging (RADAR) tracking system, a light detection and ranging (LIDAR) tracking system, an ultrasound tracking system, and any other suitable spatial measuring method. The tracking system 112 is configured to identify a face feature point. The face feature point comprises one or more of an eye center point, a nose center point, a mouth lateral point, and a mouth center point.

The robot 102 further comprises an arm 114, the arm configured to do one or more of position the mask 104 with respect to the user 109 and orient the mask 104 with respect to the user 109. The arm 114 comprises a flange 115, the flange 115 coupled to an end of the arm 114. The arm 114 can have one or more degrees of freedom. Alternatively, or additionally, the flange 115 can have one or more degrees of freedom. The arm 114 is configured to move the flange 115 along a degree of freedom. For example, the arm 114 can have seven degrees of freedom. For example, the arm 114 can have fewer degrees of freedom, for example six degrees of freedom, or more degrees of freedom, for example eight degrees of freedom. For example, the six degrees of freedom comprise one or more of three directions describing a location of the arm 114 and three directions describing an orientation of the arm 114. The robot 102 further comprises a robot base 116 configured to support the arm 114. The flange 115 is coupled to an end of the arm 114 that is distal from the robot base 116. The mask 104 is also coupled to the flange 115.

The arm 114 further comprises a kinematic mount 117, the kinematic mount 117 usable to do one or more of orient and locate the mask 104 with respect to the flange 115. Preferably, but not necessarily, the kinematic mount 117 is usable to both orient the mask with respect to the flange 115 and locate the mask 104 with respect to the flange 115. Alternatively, or additionally, the arm 114 comprises a mount other than a kinematic mount, attaching to the flange 115. The kinematic mount 117 comprises a flange kinematic mount 119, the flange kinematic mount 119 mounted to the flange 115. The kinematic mount 117 further comprises a mask system kinematic mount 120, the mask system kinematic mount 120 mounted to the mask system 103. The mask system kinematic mount 120 attaches to the flange kinematic mount 119 by a mounting feature 121. The mounting feature 121 is configured for intermittent attachment of the flange kinematic mount 119 and the mask system kinematic mount 120. For example, de-attachment of the flange kinematic mount 119 and the mask system kinematic mount 120 may be necessary for one or more of cleaning, sterilizing, sanitizing, and replacing, and the like. For example, the mask system kinematic mount 120 comprises an SB1 kinematic mount base manufactured by Thorlabs of Newton, New Jersey (www.thorlabs.com), The mounting feature 121 comprises one or more of a kinematic mounting feature 121, a magnetic mounting feature 121, a mechanical mounting feature 121, and a clamp-on mounting feature 121.

The system 100 is configured to move the arm 114 toward the face 108 of the user 109 after the face feature point is identified. The system 100 is further configured to move the arm 114 so as to bring the mask 104 into contact with the face 108 of the user 109 after the face feature point is identified.

The system 100 is further configured, following bringing the mask 104 into contact with the face 108 of the user 109, to command the arm 114 to maintain one or more of an appropriate contact force with respect to the user's face 108 and an appropriate position with respect to the user's face 108. The appropriate contact force and the appropriate position create a safe and effective contact engagement between the mask 104 and the face 108 of the user 109.

The system 100 is further configured, following bringing the mask 104 into contact with the face 108 of the user 109, to command the arm 114 to maintain both an appropriate contact force with respect to the user's face 108 and an appropriate position with respect to the user's face 108.

The system 100 is further configured, following movement of the face 108 of the user 109, to move the position of the arm 114 so as to maintain an appropriate position with respect to the user's face 108.

The system 100 is further configured, wherein following a failure of the system 100 to maintain the arm 114 at both an appropriate contact force and an appropriate position, to retract the arm 114 so as to move the mask 104 away from the face 108 of the user 109.

The system 100 is further configured, following retraction of the arm 114, to go into a mode in which the system 100 awaits entry by the user 109 into a requisite sleep state. The system 100 is further configured, upon entry by the user 109 into the requisite sleep state, to move the arm 114 toward the face 108 of the user 109.

The tracking system 112 can include one or more of a transmitter configured to transmit a signal describing a biometric signal of the user 109, a transmitter configured to transmit spatial tracking information, a camera system configured to capture image data, a tracking sensor configured to detect the signal, thereby gathering sensor data, and a processor configured to control one or more of aspect of the system 100.

The tracking system 112 comprises a tracking system coordinate frame 113. The tracking system coordinate frame 113 can be defined from a feature of the tracking system 112. For example, the coordinate system of the Intel RealSense Depth Camera D435, sold by Intel Corporation of Santa Clara, California (www.intel.com) locates and orients its camera coordinate system with respect to its left infrared camera. When tracking an object, the tracking system 112 can determine one or more of a coordinate frame and a centroid of the tracked object. When tracking an object feature, the tracking system 112 can determine one or more of a coordinate frame and a centroid of the tracked feature. The coordinate frame can be defined with respect to the tracking coordinate frame 113. Centroid tracking data can be defined with respect to the tracking coordinate frame 113.

The base 102 further comprises a controller 122 configured to control the system 100. For example, the controller 122 comprises one or more of a tracking controller configured to control the tracking system 112, a ventilator controller configured to control the ventilator 106, and another controller. The controller 122 commands the arm 114 to maintain one or more of an appropriate contact force with respect to the user's face 108 and an appropriate position with respect to the user's face 108. The controller 122 commands the arm 114 to maintain both the appropriate contact force with respect to the user's face 108 and the appropriate position with respect to the user's face 108. The controller 122 is further configured to change a pose of the mask 104 based on one or more of the image data, lapse of a predetermined period of time, and an estimated sleep state of the user 109. The estimated sleep state of the user 109 comprises one or more of the requisite sleep state and an estimation of stability of the sleep state of the user 109. The system 100 transitions from the sleep state to an approach state if the system determines that the estimated sleep state of the user 109 is the requisite sleep state and if the system further determines that the estimated sleep state of the user 109 is stable. Alternatively, or additionally, the system 100 transitions from the sleep state to a wait for sleep state in which the system 100 waits if the system 100 determines one or more of that the estimated sleep state of the user 109 is not the requisite sleep state and that the estimated sleep state of the user 109 is not stable.

The controller 122 is further configured to change a pose of the mask 104 based at least in part on biometric data from the biometric sensor system 111.

The base 102 further comprises a display 123 configured to display information to the user 109 regarding the system 100, Optionally, the display 123 includes a user interface 124. The user interface 124 can provide information to the user 109, for example, power status of the system 100. The user interface 124 can include push buttons usable by the user 109 to control the system 100.

For example, the user interface 124 comprises one or more of an indicator, a speaker, a microphone, a button, and a switch. Alternatively, or additionally, the user interface 124 comprises one or more of a standalone interface and an interface comprised in a portion of the system 100 other than the display 123.

The biometric sensor system 111 then transmits the estimated state of the user 109 to the controller 122. The controller 122 can store the estimated state of the user 109 in a database 128.

The biometric sensor system 111 receives biometric data, determines a user parameter based at least in part on the received biometric data, and estimates a state of the user 109 based at least in part on the determined parameter. The biometric sensor system 111 stores in the database 128 one or more of the biometric data, the estimated state of the user, and the determined parameter. The biometric sensor system 111 can send the biometric to the system 100 the one or more of the biometric data, the estimated state of the user, and the determined parameter.

The robot base 116 comprises a set of tube-base connections 130 through which the robot base 116 couples to the gas tube 105. For example, the set of tube-base connections 130 through which the robot base 116 couples to the gas tube 105 can include a system sensor 132 configured to gather sensor data and store gathered data in the database 128. For example, the tube-base connection 130 comprises a tube-base opening 130.

For example, the robot 102 comprises a system sensor 132 configured to sense one or more of forces, torques, currents, voltages, temperatures, and the like. For example, the arm 114 comprises the system sensor 132.

The flange 115 includes a flange-mask connection 136 through which the flange 115 couples to the mask system 103. For example, the flange-mask connection 136 comprises a flange-mask opening 136. The flange-mask connection 136 can include a robot mounting feature 138.

The flange kinematic mount 119 comprises a flange kinematic mount coordinate frame 142 which can be defined from a feature of the flange kinematic mount 119. The robot mounting feature 138 can comprise an opening (not shown). The gas 107 can pass through the opening. A signal can pass through the opening. The opening can comprise a sensor, the sensor configured to detect the gas 107.

The gas tube 105 is coupled to the robot base 116. The gas tube 105 is also coupled to the mask system 103. The gas tube 105 further includes a tube-mask connection 144 that couples the gas tube 105 to the mask system 103. Alternatively, or additionally, the mask 104 comprises the tube-mask connection 144. For example, the tube-mask connection 144 comprises a tube-mask opening 144.

The gas tube 105 can carry the gas 107 between the robot base 116 and the mask system 103 through the tube-base connection 130.

The mask system 103 can comprise the mask 104 configured to distribute the gas 107 to the user 109. The mask system 103 can be removed from the flange 115, or the flange kinematic mount 119, for example, for one or more of cleaning, sterilizing, sanitizing, and replacing, and the like.

Figure 1B:
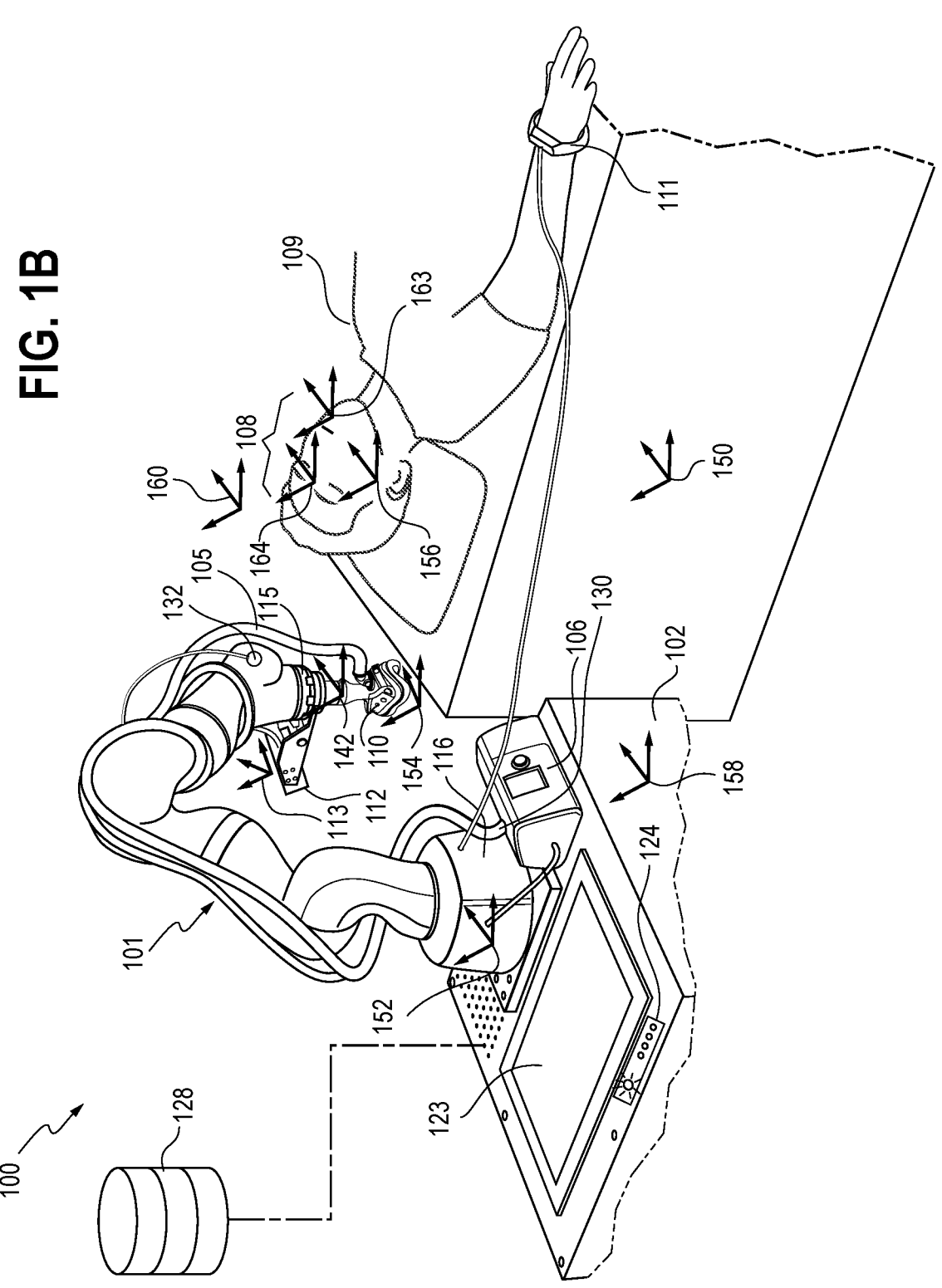
FIG. 1B is a drawing of a coordinate frame system usable with the robotic ventilation system.

FIG. 1B shows key coordinate frames of the robotic ventilation system. The coordinate frames include a world coordinate frame 150, a robot base coordinate frame 152, the flange kinematic mount coordinate frame 142, the tracking system coordinate frame 113, a mask system coordinate frame 154, a face coordinate frame 156, a system base coordinate frame 158, and a ready coordinate frame 160. These frames can represent spatial relationships and can be stored in the database 128.

The world coordinate frame 150 represents an environment reference. For example, the world coordinate frame 150 defines a common reference for all other coordinate frames.

The robot base coordinate frame 152 represents a spatial reference for the robot base 116. For example, the robot base coordinate frame 152 can be defined with respect to the robot base 116.

The flange kinematic coordinate frame 142 represents a flange 115 reference. For example, the flange kinematic coordinate frame 142 can be defined with respect to the flange 115.

The tracking system coordinate frame 113 represents a tracking system reference. For example, the tracking system coordinate frame 113 can be defined with respect to tracking system 112, and points in the tracking system coordinate frame 113 are relative to the tracking system 112.

The mask system coordinate frame 154 represents a mask reference. For example, the mask system coordinate frame 154 can be defined with respect to the mask 104.

For example, the tracking system 112 can determine the mask system coordinate frame 154 based on one or more of the mask features and a fiducial marker 110. The tracking system 112 can determine a spatial relationship of the mask system coordinate frame 154 with respect to the tracking system controller frame 113. The tracking system 112 can store the mask system coordinate frame 154 in the database 128.

The face 108 of the user 109 is represented with a face coordinate frame 156. For example, the face coordinate frame 156 can be defined with respect to a face fiducial coordinate frame 163. For example, the face coordinate frame 156 can be defined with respect to a face feature coordinate frame 164. For example, the face coordinate frame 156 can be a function of a pose of the face 108 of the user 109. For example, the face coordinate frame 156 can be defined with respect a pose of the face 108 of the user 109 at a particular point in time. For example, the face coordinate frame 156 can change as the pose of the face 108 of the user 109 changes. For example, the face coordinate frame 156 can be identical to the face fiducial coordinate frame 163. For example, the face coordinate frame 156 can comprise the face feature coordinate frame 164. The tracking system 112 can determine a transform between the face coordinate frame 156 and the mask system coordinate frame 154.

For example, the tracking system 112 can determine the face coordinate frame 156 based on one or more of a facial feature (not shown in FIG. 1B; item 407 in FIG. 4) and the fiducial marker 110. The tracking system 112 can store the face coordinate frame 156 in the database 128.

For example, the face feature coordinate frame 164 can be defined by a facial feature (not shown in FIG. 1B; item 407 in FIG. 4) of the user 109. For example, the face feature coordinate frame 164 can be a function of the pose of a face feature (not shown in FIG. 1B; item 407 in FIG. 4) of the user 109. For example, the face feature coordinate frame 164 can be defined with respect to a pose of a face feature (not shown in FIG. 1B; item 407 in FIG. 4) of the user 109 at a particular point in time. For example, the face feature coordinate frame 164 can change with respect to the tracking system 112 as the pose of the face 108 of the user 109 changes.

For example, the tracking system 112 can determine the face coordinate frame 156 based on one or more of the face feature coordinate frame 164 and the face fiducial coordinate frame 163. For example, the tracking system 112 can determine the face feature coordinate frame 164. Alternatively, or additionally, the tracking system 112 can determine the face fiducial coordinate frame 163. Alternatively, or additionally, the tracking system 112 can determine the face coordinate frame 156. For example, the tracking system 112 can determine the face coordinate frame 156 based on one or more of the determined/defined face feature coordinate frame 164 and the determined/defined face fiducial coordinate frame 163. For example, the tracking system 112 can access the face feature coordinate frame 164 in the database 128. Alternatively, or additionally, the tracking system 112 can access the face fiducial coordinate frame 163 in the database 128. Alternatively, or additionally, the tracking system 112 can determine the face coordinate frame 156. For example, the tracking system 112 can determine the face coordinate frame 156 based on one or more of the face feature coordinate frame 164 and the face fiducial coordinate frame 163.

One or more of the face coordinate frame 156, the face fiducial coordinate frame 163 and the face feature coordinate frame 164 can be tracked by the tracking system 112. The controller 122 can use the one or more of the face coordinate frame 156, the face fiducial coordinate frame 163 and the face feature coordinate frame 164 as a spatial reference to do one or more of correctly locate the mask 104 and place the mask 104 on the face 108 of the user 109.

The system base coordinate frame 158 represents a system base reference. For example, the system base coordinate frame 158 can be defined with respect to the robot base 116. For example, points in the system base coordinate frame 158 are defined relative to the robot base 116.

For example, the ready coordinate frame 160 represents a taught reference that can be learned and maintained. For example, the ready coordinate frame 160 can be defined with respect to the mask 104. For example, the ready coordinate frame 160 can be defined when the face 108 of the user 109 is in the field of view of the tracking system 112. In this example, the system controller 122 can wait for the user 109 to enter a requisite sleep state.

The tracking system 112 can determine spatial relationships between two or more bodies in space. For example, the tracking system 112 can determine a spatial relationship between a first body in space and a second body in space. For example, the tracking system 112 can define a first coordinate frame for the first body in space. For example, the tracking system 112 can define a second coordinate frame for the second body in space. The tracking system 112 can then determine a transform between the first coordinate frame and the second coordinate frame, the transform describing a spatial relationship between the first body in space and the second body in space. The tracking system 112 can determine a transform between the face coordinate frame 156 and the mask system coordinate frame 154. The tracking system 112 can use chaining to determine the spatial relationships. The tracking system 112 can store the transform between the first coordinate frame and the second coordinate frame in the database 128.

Figure 2:
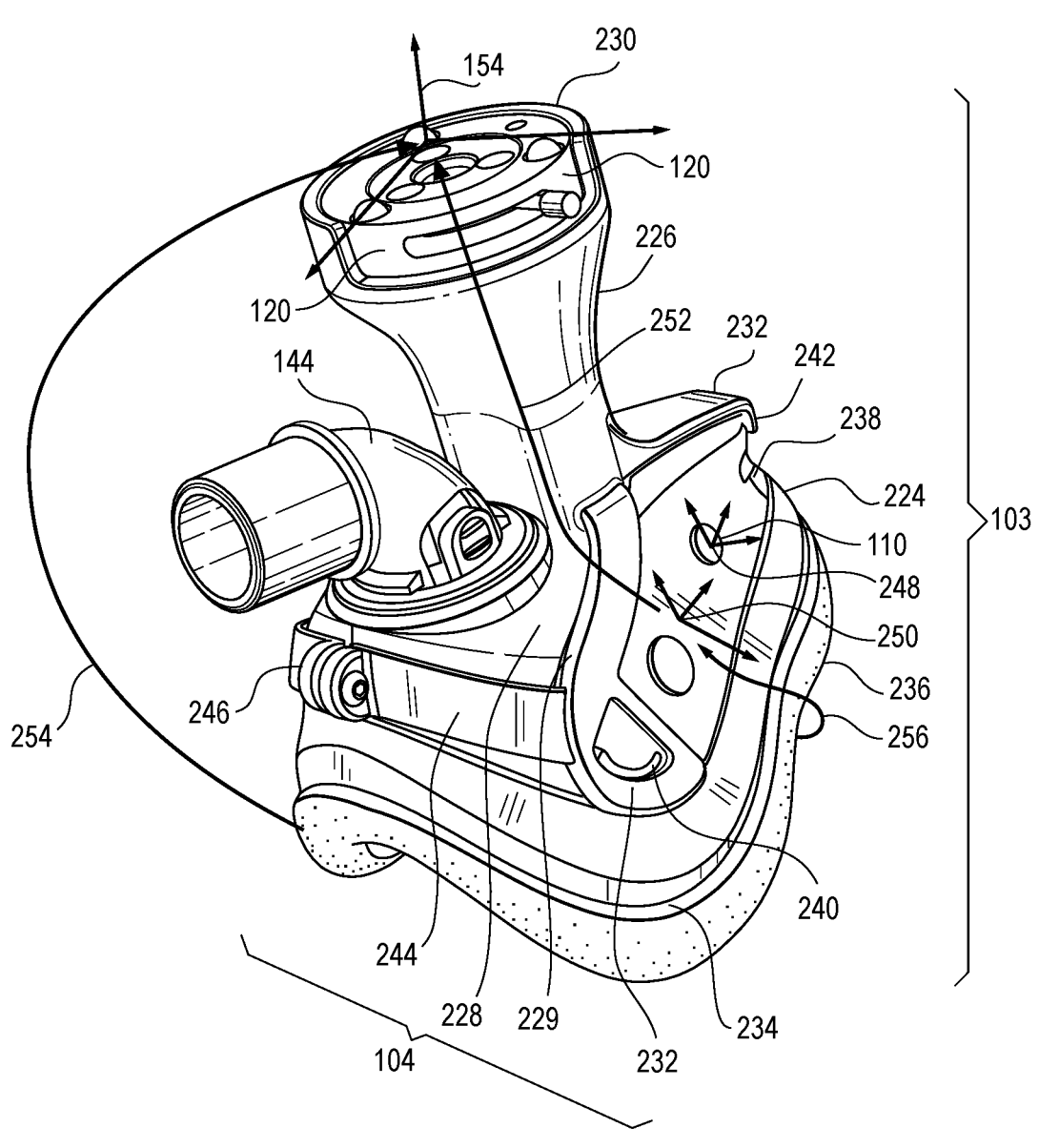
FIG. 2 is a drawing of a mask system of the robotic ventilation system.

FIG. 2 is a drawing of the mask system 103 of the robotic ventilation system 100. The mask system 103 again comprises the mask 104 and the fiducial marker 110. As depicted, the mask 104 further comprises the tube-mask connection 144.

As depicted, the mask system 103 further comprises a housing 224. The mask system 103 further comprises a facial interface stem 226, the facial interface stem 226 configured to offset the mask 104 to provide clearance for the mask-tube connection 144. The mask 104 further comprises a mask stem 228 configured to protrude through a mask stem opening 229 to enable clamping. The facial interface stem 226 comprises a stem-flange connection 230 through which the facial interface stem 226 couples to the flange 115. For example, the stem-flange connection 230 comprises a stem-flange opening 230. Optionally, a single connection (not shown) comprises both the tube-mask connection 144 and the stem-flange connection 230.

The mask system 103 further comprises a mask mounting feature 232 usable to mount the mask 104 to the facial interface stem 226. Preferably, but not necessarily, the mask mounting feature 232 is rigidly fixed to the mask stem 228. The mask mounting feature 232 is usable to locate the mask 104 with respect to the flange 115. Alternatively, or additionally, the mask mounting feature 232 is usable to orient the mask 104 with respect to the flange 115. The mask mounting feature 232 comprises one or more of the mask system mounting feature 232, a magnetic mask system mounting feature 232, a mechanical mask mounting feature, and a clamp-on mask mounting feature.

The mask 104 can be coupled to the flange 115 via the mask mounting feature 232. For example, the mask mounting feature 232 can engage with the robot mounting feature 138. The mask mounting feature 232 allows for a repeatable mechanical connection between the mask 104 and the flange 115.

The mask 104 can further comprise a contact edge 234. The contact edge 234 comprises a mask seal 236. The mask seal 236 covers the contact edge 234. The contact edge 234 can be substantially rigid. The mask seal 236 can comprise one or more of an inflatable bladder and a soft deformable material. The mask seal 236 is configured to conform to the face of the user. The mask seal 236 is further configured to facilitate formation of an effective seal against the face of the user during use. The mask seal 236 ensures secure delivery to the user of correctly pressurized gas 107.

Optionally, the mask 104 and the facial interface stem 226 are separable components. In other words, the mask 104 and the mask stem 228 can be detached from one another. The mask 104 and the mask stem 228 can be coupled using a coupling mechanism.

The mask 104 further comprises a groove 238 configured to engage with the mask mounting feature 232. Optionally, and as depicted, the mask 104 can further include a wing 240 configured to engage with the mask mounting feature 232. As depicted, the wing 240 extends outward from the mask 104. The mask system 103 further comprises a protrusion 242 configured to engage with the groove 238. Optionally, and as depicted, the facial interface stem 226 further comprises a clamping portion 244 configured to clamp the mask stem 228. Optionally, and as depicted, the facial interface stem 226 further comprise a screw portion 246 usable to do one or more of clamp the mask stem 228 and further clamp the mask stem 228. The screw portion 246 is configured to clamp the mask stem 228 via tightening of the screw portion 246.

If the screw portion 246 is engaged to tighten the contact between the clamping portion 244 and the wing 240, the mask stem 228 and the mask 104 can be effectively coupled together. If the screw portion. is disengaged to loosen the contact between the clamping portion 244 and the wings 240, the mask stem 228 and the mask 104 can be separated from one another by disengaging the contact between clamping portions 222 and the wings 218, and by disengaging the protrusion 242 from the groove 238.

The fiducial marker 110 comprises a fiducial marker coordinate frame 248. The fiducial marker 110 can be tracked by the tracking system 112. The fiducial marker 110 can serve as a tracking reference for the tracking system 112. The fiducial marker coordinate frame 248 can be defined by features of the fiducial marker 110. For example, the open source ArUco library (Universitario de Rabanales, University of Córdoba, 14071, Córdoba, Spain) (www.uco.es) includes numerous fiducial marker designs with coordinate frames defined from the design features.

A mask system fiducial marker coordinate frame 250 can be defined with respect to the mask system coordinate frame 154. Alternatively, or additionally, the mask system fiducial marker coordinate frame 250 can be defined with respect to the fiducial marker coordinate frame 248. For example, a measuring tool can be used such as the Gauge Max Faro Arm, manufactured by Faro Technologies, Inc. of Lake Mary, Florida (www.faro.com). Alternatively, or additionally, the spatial relationship 250 may be incorporated into the mask 104 during construction of the mask 104. The mask system coordinate frame can be stored in the database.

A spatial relationship 252 of the fiducial marker coordinate frame 248 can be defined with respect to the mask system coordinate frame 154. Alternatively, or additionally, the spatial relationship 252 may be incorporated into the mask system 103 during construction.

A spatial relationship 254 of the mask seal 236 can be defined with respect to the mask system coordinate frame 154. Alternatively, or additionally, the spatial relationship 254 may be incorporated into the mask system 103 during construction.

A spatial relationship 256 of the fiducial marker coordinate 248 frame can be defined with respect the mask seal 236. Alternatively, or additionally, the spatial relationship 230 may be incorporated into the mask 104 during construction of the mask 104.

Figure 3:
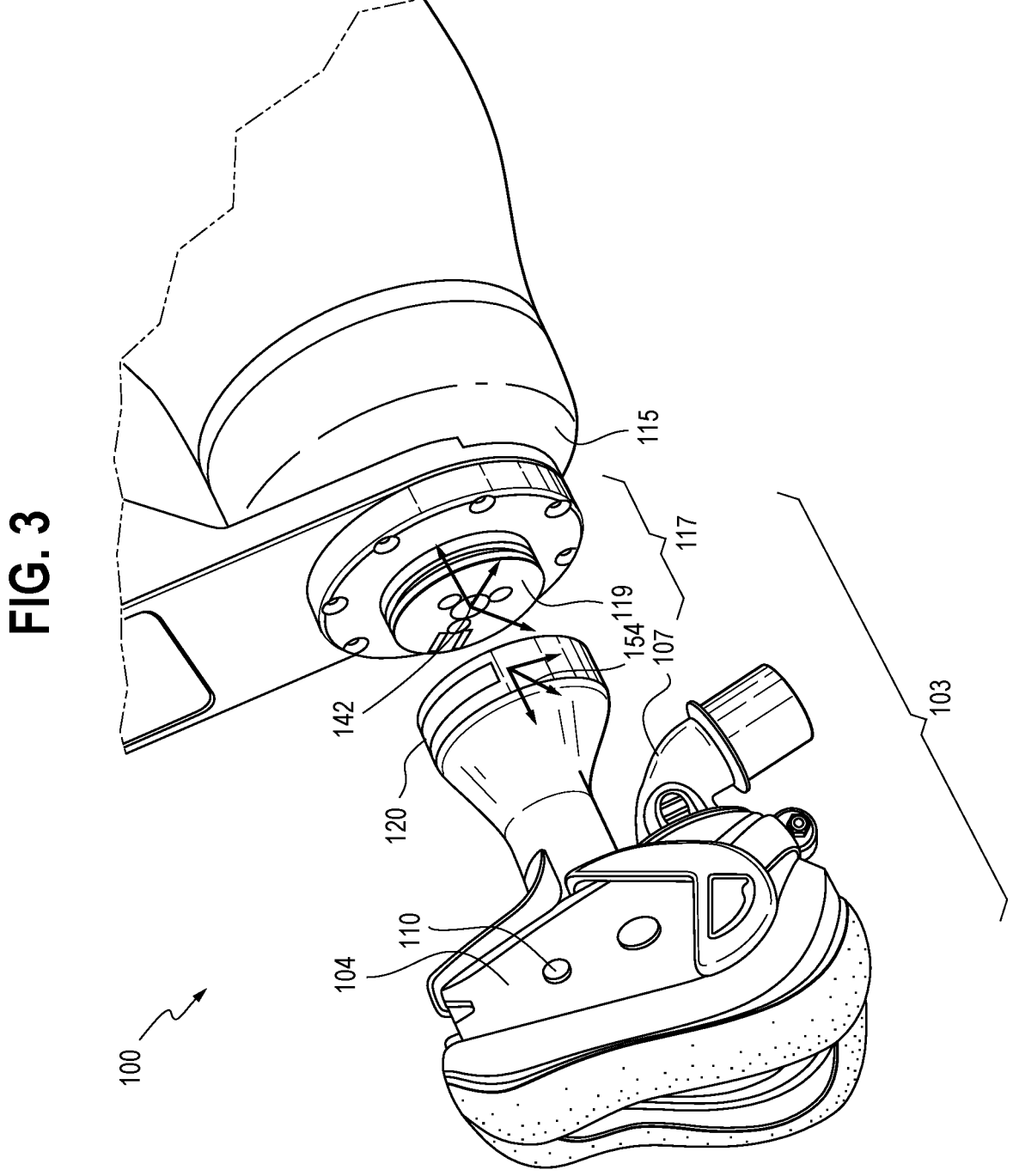
FIG. 3 is a drawing of a detail of the robotic ventilation system, showing the mask system attaching to a flange via a kinematic mount.

FIG. 3 is a drawing of a detail of the robotic ventilation system 100, showing the mask system 103 attaching to the flange 115 via the kinematic mount 117.

FIG. 3 shows the mask system 103 comprising the mask 104 and the fiducial marker 110. The kinematic mount 117 again comprises the flange kinematic mount 119 and the mask system kinematic mount 120. FIG. 3 also shows the arm 114 that is distal from the robot base (not shown in this figure; item 116 in FIG. 1A). The arm 114 comprises the flange 115. The flange 115 in turn comprises the flange kinematic mount 119. Preferably, but not necessarily, the flange kinematic mount 119 is rigidly fixed relative to the flange 115. The flange kinematic mount 119 can engage with the mask system kinematic mount 120 to do one or more of locate and orient the mask 104 with respect to the flange 115.

The flange kinematic mount 119 comprises a flange kinematic mount coordinate frame 142. When coupled, there can be a fixed spatial relationship between the flange coordinate frame 142 and the mask system kinematic mount coordinate frame 154. The flange kinematic mount 119 allows for creation of a repeatable mechanical connection between the mask system 103 and the flange 115 such that when the mask system 103 is removed from a first mask position and then reattached, the mask system 103 goes back into the same first mask position with respect to the flange 115 in a repeatable, predictable manner. Alternatively, or additionally, the mask system 103 that is removed can be a distinct mask system 103 from the mask system that is later reattached.

Figure 4:
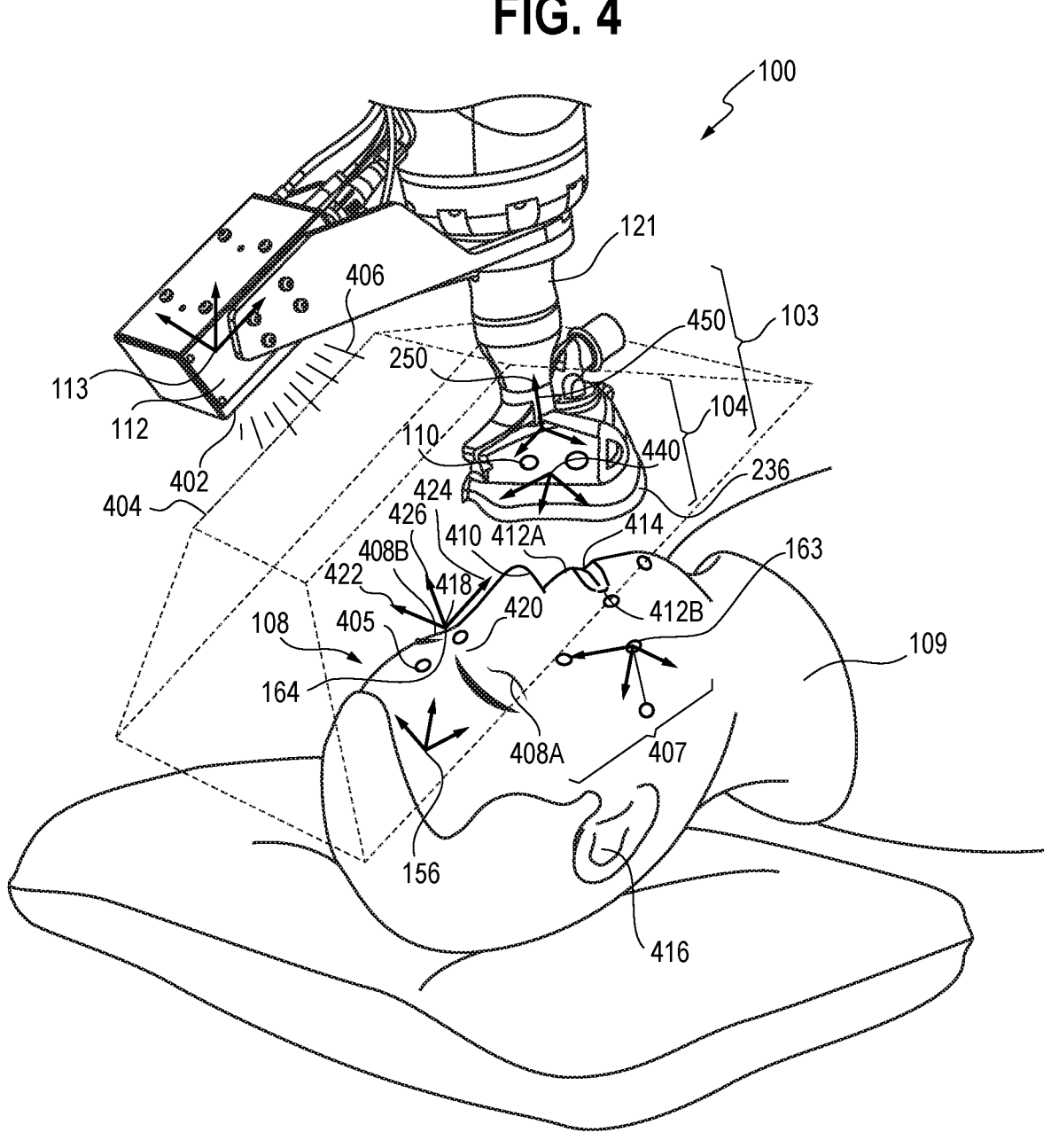
FIG. 4 is a drawing of the robotic ventilation system in use on behalf of a user.

FIG. 4 is a drawing of the robotic ventilation system 100 in use on behalf of a user 109. Shown again are the mask system 103, the mask 104, the face 108 of the user 109, the fiducial marker 110, and the tracking system 112. The tracking system 112 comprises an imaging device 402 configured to image objects. The tracking system is configured to image objects within a field of view 404. Optionally, and as depicted, the system 100 further comprises a facial fiducial marker 405. The facial fiducial marker 405 comprises a tracked object 405 placed on the face 108 of the user 109 at a known pose in a field of view 404 of the tracking system 112 that can be viewed by the tracking system 112 and can serve as a reference for the tracking system 112. For example, the face 108 of the user 109 can have a facial fiducial marker 405 affixed in a suitable manner to allow for tracking by the tracking system 112 while the mask 104 is adjacent to the face 108 of the user 109.

For example, when the face 108 of the user 109 is within the field of view 404 of the tracking system 112 and contains three or more facial fiducial markers 405, the tracking system can determine a face fiducial coordinate frame 163.

The tracking system 112 further comprises a light source 406 configured to generate light. Optionally, the tracking system further comprises a processor (not shown). The light source 406 emits light in an area that at least overlaps with the field of view 404 of the imaging device 402. The tracking system 112 can determine a spatial relationship between the tracking system coordinate frame 113 and a centroid of the tracked body, and can store the spatial relationship in the database. Additionally, or alternatively, the tracking system 112 can determine a coordinate frame of the tracked body using at least three spatial centroid points. The tracking system can then store the coordinate frame spatial relationship in the database. For example, a camera can be used such as the OAK-D stereo camera system manufactured by Luxonis Holding Corporation of Westminster, Colorado (www.luxonis.com).

The tracking system 112 can instruct the imaging device 402 to capture one or more images. The tracking system 112 can store the image data in the database.

The tracking system 112 processes the captured images with an image processing technique to track the facial fiducial marker 405. The tracking system 112 stores in the database a relative spatial relationship of the fiducial marker coordinate frame 248 with respect to the tracking system coordinate frame 113.

The tracking system 112 processes the captured images with an image processing technique. The tracking system 112 can track a facial feature 407 of the face 108 of the user 109. The tracking system 112 can store in the database a relative spatial relationship of the centroid point with respect to the tracking system coordinate frame 113.

The tracking system 112 can track an object feature point of a tracked object. The tracking system 112 can store in the database the relative spatial relationship of the feature point with respect to the tracking system coordinate frame 113.

During use, the field of view 404 can envelop the face 108 of the user 109 such that the tracking system 112 can track a facial feature 407 of the face 108 of the user 109. The facial feature 407 comprises one or more of a left eye 408A, a right eye 408B, a nose 410, a mouth left lateral 412A, a mouth right lateral 412B, a mouth center 414, a left ear (not shown), and a right ear 416. For example, the left eye 408A comprises a left eye point 408A. For example, the right eye 408B comprises a right eye point 408B. For example, the nose 410 comprises a nose point 410. For example, the mouth left lateral 412A comprises a mouth left lateral point 412A. For example, the mouth right lateral 412B comprises a mouth right lateral 412B. For example, the mouth center 414 comprises a mouth center point. For example, the left ear (not shown) comprises a left ear point (not shown). For example, the right ear 416 comprises a right ear point 416. For example, the left eye 408A comprises a left eye centroid point 408A. For example, the right eye 408B comprises a right eye centroid point 408B. For example, the nose 410 comprises a nose centroid point 410. For example, the mouth left lateral 412A comprises a mouth left lateral centroid point 412A. For example, the mouth right lateral 412B comprises a mouth right lateral centroid 412B. For example, the mouth center 414 comprises a mouth center centroid point. For example, the left ear (not shown) comprises a left ear centroid point (not shown). For example, the right ear 416 comprises a right ear centroid point 416.

One or more of the eye centroid points 408A-408B and the nose point 410 can be used to form a face feature coordinate frame 164. A face feature coordinate frame origin 418 can be located at the midpoint 420 of a line defined from the eye point 408A to the eye point 408B. A face feature coordinate frame X axis 422 can be the normalized line from the midpoint 420 to the eye point 408B. The face feature coordinate frame Y axis 424 can be the normalized line from the midpoint 420 to the nose point 410. A face feature coordinate frame Z axis 426 can be defined from the normalized cross product of the face feature coordinate frame X axis 422 with the face feature coordinate frame Y axis 424. These calculations can be performed by the tracking system 112 to determine a spatial relationship of the face feature coordinate frame 164 with respect to the tracking system coordinate frame 113. The tracking system 112 can store the face feature coordinate frame 164 in the database.

For example, the mask system 103 with an attached fiducial marker 110 can be in the field of view 404. When at least three or more fiducial markers 110 are viewable, the tracking system can determine a mask fiducial coordinate frame 440. The spatial relationship of the face fiducial coordinate frame 440 with the tracking system coordinate frame 113 can be stored in the database.

When the user's face 108 is within the field of view 404 of the tracking system 112, and the tracking system 112 has determined the spatial relationship of the face feature coordinate frame 164, the controller 122 can instruct the arm 114 to orient the mask 104 so as to maintain a specified spatial relationship of the mask seal 236 with respect to the facial feature coordinate frame 416. The specified spatial relationship can be computed by the controller 122. Alternatively, or additionally, the specified spatial relationship is received from the user 109. The controller 122 can instruct the arm 114 to maintain one or more of a specified contact force and a specified contact torque of the mask seal 236 with respect to the user's face 108. This mode of operation is commonly referred to as hybrid position-force control.

For example, when the user's face 108 is within the field of view 404 of the tracking system 112, and the tracking system 112 has determined the spatial relationship of the face fiducial coordinate frame 163, the controller 122 can instruct the arm 114 to orient the mask 104 so as to maintain a specified spatial relationship of the mask seal 236 with respect to the face fiducial coordinate frame 163. Alternatively, or additionally, the controller 122 can instruct the arm 114 to maintain specified contact forces and torques of the mask seal 236 with respect to the user's face 108. This mode of operation is commonly referred to as hybrid position-force control.

FIG. 5 is a flow chart of a method 500 for correct mask placement using a robotic ventilation system including a kinematic mount.

The order of the steps in the method 500 is not constrained to that shown in FIG. 5 or described in the following discussion. Several of the steps could occur in a different order without affecting the final result.

In step 510, image data is captured, the image data comprising a facial feature of a user, by a system comprising: a robot comprising an arm, the arm comprising a flange, the flange coupled to an end of the arm, the arm configured to move the flange along a degree of freedom; a mask coupled to the flange, the mask configured to deliver gas to a user, wherein the arm further comprises a kinematic mount, the kinematic mount usable to do one or more of orient and locate the mask with respect to the flange; a ventilator coupled to the mask, the ventilator configured to deliver the gas to the mask; a gas tube coupled to both the mask and the ventilator, the gas tube configured to carry gas between the ventilator and the mask; a controller configured to change a pose of the mask, the controller further configured to control the delivery of the gas from the ventilator to the user; and a tracking system, the tracking system configured to capture image data of one or more of the mask and a face of the user, wherein the controller is configured to change the mask pose based at least in part on the image data. For example, the tracking system captures the image data, the image data comprising the facial feature of the user. Optionally, the image data further comprises image data regarding the fiducial marker. Optionally, the image data further comprises image data regarding a facial fiducial marker comprised in the user's face. Block 510 then transfers control to block 520.

In step 520, by the system, the facial feature of the user is tracked. Optionally, the system further tracks the facial fiducial marker. Block 520 then transfers control to block 530.

In step 530, by the system, a face coordinate frame is determined with respect to the user's face. The system can store the face coordinate frame. For example, the tracking system can store the face coordinate frame in the database. Block 530 then transfers control to block 540.

In step 540, by the system, a mask system coordinate frame is determined with respect to the mask. The system can store the mask system coordinate frame. For example, the tracking system can store the mask system coordinate frame in the database. Block 540 then transfers control to block 550.

In step 550, by the system, a transform is determined between the face coordinate frame and the mask system coordinate frame. For example, the tracking system determines the transform between the face coordinate frame and the mask system coordinate frame. Block 550 then transfers control to block 560.

At step 560, by the system, the transform is stored as a spatial relationship between the facial coordinate system and the mask coordinate system, the spatial relationship configured for correct placement of the mask on the user's face. Preferably, but not necessarily, the tracking system stores the transform as the spatial relationship between the facial coordinate system and the mask coordinate system. Block 560 then terminates the process.

FIG. 6 is a flow chart of a method 600 for correct mask placement using a robotic ventilation system including a fiducial marker.

The order of the steps in the method 600 is not constrained to that shown in FIG. 6 or described in the following discussion. Several of the steps could occur in a different order without affecting the final result.

In step 610, image data is captured, the image data comprising a facial feature of a user, the image data further comprising image data regarding the fiducial marker, by a system comprising: a robot comprising an arm, the arm comprising a flange, the flange coupled to an end of the arm, the arm configured to move the flange along a degree of freedom; a mask coupled to the flange, the mask configured to deliver gas to a user, the mask comprising a fiducial marker; a ventilator coupled to the mask, the ventilator configured to deliver the gas to the mask; a gas tube coupled to both the mask and the ventilator, the gas tube configured to carry the gas between the ventilator and the mask; a controller configured to change a pose of the mask, the controller further configured to control the delivery of the gas from the ventilator to the user; and a tracking system, the tracking system configured to capture image data of one or more of the mask and a face of the user, the tracking system further configured to track the fiducial marker, wherein the controller is configured to change the mask pose based at least in part on the image data. For example, the tracking system captures the image data, the image data comprising the facial feature of the user. Block 610 then transfers control to block 620.

In step 620, by the system, the facial feature of the user is tracked and the fiducial marker is tracked. Optionally, the system further tracks the facial fiducial marker. Block 620 then transfers control to block 630.

In step 630, by the system, a face coordinate frame is determined with respect to the user's face. The system can store the face coordinate frame. For example, the tracking system can store the face coordinate frame in the database. Block 630 then transfers control to block 640.

In step 640, by the system, a mask system coordinate frame is determined with respect to the mask. The system can store the mask system coordinate frame. For example, the tracking system can store the mask system coordinate frame in the database. Block 640 then transfers control to block 650.

In step 650, by the system, a transform is determined between the face coordinate frame and the mask system coordinate frame. For example, the tracking system determines the transform between the face coordinate frame and the mask system coordinate frame. Block 650 then transfers control to block 660.

At step 660, by the system, the transform is stored as a spatial relationship between the facial coordinate system and the mask coordinate system, the spatial relationship configured for correct placement of the mask on the user's face. Preferably, but not necessarily, the tracking system stores the transform as the spatial relationship between the facial coordinate system and the mask coordinate system. Block 660 then terminates the process.

FIG. 7 is a flow chart of a method 700 for correct mask placement using a robotic ventilation system including a kinematic mount and further including a fiducial marker.

The order of the steps in the method 700 is not constrained to that shown in FIG. 7 or described in the following discussion. Several of the steps could occur in a different order without affecting the final result.

In step 710, image data is captured, the image data comprising a facial feature of a user, by a system comprising: a robot comprising an arm, the arm comprising a flange, the flange coupled to an end of the arm, the arm configured to move the flange along a degree of freedom, the arm further comprising a kinematic mount; a mask coupled to the flange by a mounting feature configured for intermittent attachment, the mask configured to deliver gas to a user, wherein the kinematic mount is usable to do one or more of orient and locate the mask with respect to the flange; a mask coupled to the robot, wherein the mask is coupled to the flange by a mounting feature configured for intermittent attachment, the mounting feature comprising the kinematic mount, the mounting feature further comprising an opening, wherein the mounting feature further comprises a sensor, the sensor configured to verify that proper seating has occurred of the mask on the user, wherein a spatial alignment of the mask with respect to the kinematic mount is known a priori, wherein the mask further comprises a fiducial marker, the fiducial marker configured to be tracked by a tracking system; a ventilator coupled to the mask, the ventilator configured to deliver the gas to the mask, wherein the gas passes through the opening, wherein the opening comprises a sensor, the sensor configured to detect the gas; a gas tube coupled to both the mask and the ventilator, the gas tube configured to carry the gas between the ventilator and the mask; a controller configured to change a pose of the mask, the controller further configured to control the delivery of the gas from the ventilator to the user, wherein following a start of delivery of pressurized gas to the user, the controller commands the arm to maintain both an appropriate contact force with respect to the user's face and an appropriate position with respect to the user's face, wherein the appropriate contact force and the appropriate position create a safe and effective contact engagement between the mask and the face of the user, wherein following a failure of the system to maintain the arm at both an appropriate contact force and an appropriate position, the system is configured to retract the arm so as to move the mask away from the face of the user, wherein the system is further configured, following retraction of the arm, to go into a mode in which the system awaits entry by the user into a requisite sleep state, wherein upon entry by the user into the requisite sleep state, the system moves the arm toward the face of the user; a tracking system, the tracking system configured to capture image data of one or more of the mask and a face of the user, the tracking system configured to identify a face feature point, wherein the face feature point comprises one or more of an eye center point, a nose center point, a mouth lateral point, and a mouth center point, wherein the system moves the arm toward the face of the user after the face feature point is identified, wherein the controller is configured to change the mask pose based on one or more of the image data, lapse of a predetermined period of time, and an estimated sleep state of the user, wherein the predetermined period of time represents an indication by the user to the system that the user is going to sleep after the predetermined period of time, wherein the estimated sleep state comprises one or more of a requisite sleep state and an estimation of stability of the user's sleep state, wherein the system places the mask on the face of the user after the predetermined period of time has lapsed, the robot comprising the tracking system; and a biometric sensor system, the biometric sensor system comprising a biometric sensor, wherein the controller is further configured to change the pose of the mask based at least in part on biometric data from the biometric sensor system. For example, the tracking system captures the image data, the image data comprising the facial feature of the user. Optionally, the image data further comprises image data regarding the fiducial marker. Optionally, the image data further comprises image data regarding a facial fiducial marker comprised in the user's face. Block 710 then transfers control to block 720.

In step 720, by the system, the facial feature of the user is tracked and the fiducial marker is tracked. Optionally, the system further tracks the facial fiducial marker. Block 720 then transfers control to block 730.

In step 730, by the system, a face coordinate frame is determined with respect to the user's face. The system can store the face coordinate frame. For example, the tracking system can store the face coordinate frame in the database. Block 730 then transfers control to block 740.

In step 740, by the system, a mask system coordinate frame is determined with respect to the mask. The system can store the mask system coordinate frame. For example, the tracking system can store the mask system coordinate frame in the database. Block 740 then transfers control to block 750.

In step 750, by the system, a transform is determined between the face coordinate frame and the mask system coordinate frame. For example, the tracking system determines the transform between the face coordinate frame and the mask system coordinate frame. Block 750 then transfers control to block 760.

At step 760, by the system, the transform is stored as a spatial relationship between the facial coordinate system and the mask coordinate system, the spatial relationship configured for correct placement of the mask on the user's face. Preferably, but not necessarily, the tracking system stores the transform as the spatial relationship between the facial coordinate system and the mask coordinate system. Block 760 then terminates the process.

The foregoing description of the embodiments of the disclosure has been presented for the purpose of illustration; it is not intended to be exhaustive or to limit the disclosure to the precise form disclosed. Persons skilled in the relevant art can appreciate that many modifications and variations are possible in light of the above disclosure.

Any steps, operations, or processes described herein may be performed or implemented with one or more hardware or software modules, alone or in combination with other devices. For example, a software module is implemented with a computer program product including a computer-readable medium containing computer program code, which can be executed by a computer processor for performing any or all of the steps, operations, or processes described.

Embodiments of the disclosure can also relate to an apparatus for performing the operations herein. This apparatus can be specially constructed for the required purposes, and/or it can include a general-purpose computing device selectively activated or configured by a computer program stored in the computer. Such a computer program can be stored in a non-transitory, tangible computer readable storage medium, or any type of media suitable for storing electronic instructions, which can be coupled to a computer system bus. Furthermore, any computing systems referred to in the specification can include a single processor or can be architectures employing multiple processor designs for increased computing capability.

Throughout this specification, although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Finally, the language used in the specification has been principally selected for readability and instructional purposes, and it may not have been selected to delineate or circumscribe the disclosure. It is therefore intended that the scope of the disclosure be limited not by this detailed description, but rather by any claims that issue on an application based hereon. Accordingly, the disclosure of the embodiments of the disclosure is intended to be illustrative, but not limiting, of the scope of the disclosure, which is set forth in the following claims.

The invention claimed is:

1. A robotic ventilation system for correct mask placement comprising a kinematic mount, comprising:

a robot comprising an arm, the arm comprising a flange, the flange coupled to an end of the arm, the arm configured to move the flange along a degree of freedom;

a mask coupled to the flange, the mask configured to deliver gas to a user, wherein the arm further comprises the kinematic mount, the kinematic mount usable to do one or more of orient and locate the mask with respect to the flange;

a ventilator coupled to the mask, the ventilator configured to deliver the gas to the mask;

a gas tube coupled to both the mask and the ventilator, the gas tube configured to carry gas between the ventilator and the mask;

a controller configured to change a pose of the mask, the controller further configured to control the delivery of the gas from the ventilator to the user; and a tracking system, the tracking system configured to capture image data of one or more of the mask and a face of the user, wherein the controller is configured to change the mask pose based at least in part on the image data, wherein the tracking system is configured to identify a face feature point, wherein the face feature point comprises one or more of an eye center point, a nose center point, a mouth lateral point, and a mouth center point, wherein the system is configured to move the arm so as to bring the mask toward the face of the user, wherein the system is configured to move the arm so as to bring the mask into contact with the face of the user, wherein following bringing the mask into contact with the face of the user, the system commands the arm to maintain one or more of an appropriate contact force with respect to the user's face and an appropriate position with respect to the user's face.

2. A robotic ventilation system for correct mask placement comprising a kinematic mount, comprising:

a robot comprising an arm, the arm comprising a flange, the flange coupled to an end of the arm, the arm configured to move the flange along a degree of freedom;

a mask coupled to the flange, the mask configured to deliver gas to a user, wherein the arm further comprises the kinematic mount, the kinematic mount usable to do one or more of orient and locate the mask with respect to the flange;

a ventilator coupled to the mask, the ventilator configured to deliver the gas to the mask;

a gas tube coupled to both the mask and the ventilator, the gas tube configured to carry gas between the ventilator and the mask;

a controller configured to change a pose of the mask, the controller further configured to control the delivery of the gas from the ventilator to the user; and a tracking system, the tracking system configured to capture image data of one or more of the mask and a face of the user, wherein the controller is configured to change the mask pose based at least in part on the image data, wherein the tracking system is configured to identify a face feature point, wherein the face feature point comprises one or more of an eye center point, a nose center point, a mouth lateral point, and a mouth center point, wherein the system is configured to move the arm so as to bring the mask toward the face of the user, wherein the system is configured to move the arm so as to bring the mask into contact with the face of the user wherein following bringing the mask into contact with the face of the user, the system commands the arm to maintain both an appropriate contact force with respect to the user's face and an appropriate position with respect to the user's face.

3. The system of claim 1, wherein following movement of the face of the user, the system is configured to move the position of the arm so as to maintain an appropriate position with respect to the user's face.

4. The system of claim 1, wherein following movement of the face of the user, the arm is configured to change the contact force to maintain an appropriate contact force against the user's face.

5. The system of claim 1, wherein following a failure of the system to maintain the arm at both an appropriate contact force and an appropriate position, the system is configured to retract the arm so as to move the mask away from the face of the user.

6. The system of claim 5, wherein the system is configured, following retraction of the arm, to go into a mode in which the system awaits entry by the user into a requisite sleep state.

7. The system of claim 6, wherein upon entry by the user into the requisite sleep state, the system moves the arm toward the face of the user.

8. The system of claim 2, wherein the appropriate contact force and the appropriate position create a contact engagement between the mask and the face of the user.

9. The system of claim 2, wherein the system is configured to change the pose of the mask based on one or more of the image data, lapse of a predetermined period of time, and an estimated sleep state of the user.

10. The system of claim 9, wherein the predetermined period of time represents an indication by the user to the system that the user is going to sleep after the predetermined period of time.

11. The system of claim 10, wherein the system places the mask on the face of the user after the predetermined period of time has lapsed.

12. The system of claim 9, wherein the estimated sleep state comprises one or more of a requisite sleep state and an estimation of stability of the user's sleep state.

13. The system of claim 12, wherein the system transitions from the sleep state to an approach state if the system determines that the estimated sleep state of the user is the requisite sleep state and if the system further determines that the estimated sleep state of the user is stable.

14. The system of claim 9, wherein the system transitions from the sleep state to a wait for sleep state in which the system waits if the system determines one or more of that the estimated sleep state of the user is not the requisite sleep state and that the estimated sleep state of the user is not stable.

15. A robotic ventilation system for correct mask placement comprising a kinematic mount, comprising:

a robot comprising an arm, the arm comprising a flange, the flange coupled to an end of the arm, the arm configured to move the flange along a degree of freedom;

a mask coupled to the flange, the mask configured to deliver gas to a user, wherein the arm further comprises the kinematic mount, the kinematic mount usable to do one or more of orient and locate the mask with respect to the flange;

a ventilator coupled to the mask, the ventilator configured to deliver the gas to the mask;

a gas tube coupled to both the mask and the ventilator, the gas tube configured to carry gas between the ventilator and the mask;

a controller configured to change a pose of the mask, the controller further configured to control the delivery of the gas from the ventilator to the user;

a tracking system, the tracking system configured to capture image data of one or more of the mask and a face of the user, wherein the controller is configured to change the mask pose based at least in part on the image data, wherein the controller commands the arm to maintain one or more of an appropriate contact force with respect to the user's face and an appropriate position with respect to the user's face.

16. A robotic ventilation system for correct mask placement comprising a fiducial marker, comprising:

a robot comprising an arm, the arm comprising a flange, the flange coupled to an end of the arm the arm configured to move the flange along a degree of freedom;

a mask coupled to the flange, the mask configured to deliver gas to a user, the mask comprising the fiducial marker;

a ventilator coupled to the mask, the ventilator configured to deliver the gas to the mask;

a gas tube coupled to both the mask and the ventilator, the gas tube configured to carry the gas between the ventilator and the mask;

a controller configured to change a pose of the mask, the controller further configured to control the delivery of the gas from the ventilator to the user; and a tracking system, the tracking system configured to capture image data of one or more of the mask and a face of the user, the tracking system further configured to track the fiducial marker, wherein the controller is configured to change the mask pose based at least in part on the image data, wherein the system is configured to automatically deliver the breathable gas to the user after detecting a state of the user, wherein the state of the user comprises a requisite sleep state of the user, wherein the requisite sleep state is one or more of predetermined by the user and is determined by the system, wherein the system delivers the breathable gas to the user after fulfillment of a time-based condition, wherein the system delivers the breathable gas to the user after one or more of passage of a predetermined amount of time and after a predetermined time of day is reached, wherein the robot comprises the tracking system, wherein the tracking system is configured to identify a face feature point, wherein the system moves the arm so as to bring the mask into contact with the face of the user after the face feature point is identified, wherein following bringing the mask into contact with the face of the user, the system commands the arm to maintain one or more of an appropriate contact force with respect to the user's face and an appropriate position with respect to the user's face.

17. A robotic ventilation system for correct mask placement comprising a fiducial marker, comprising:

a robot comprising an arm, the arm comprising a flange, the flange coupled to an end of the arm the arm configured to move the flange along a degree of freedom;

a mask coupled to the flange, the mask configured to deliver gas to a user, the mask comprising the fiducial marker;

a ventilator coupled to the mask, the ventilator configured to deliver the gas to the mask;

a gas tube coupled to both the mask and the ventilator, the gas tube configured to carry the gas between the ventilator and the mask;

a controller configured to change a pose of the mask, the controller further configured to control the delivery of the gas from the ventilator to the user; and a tracking system, the tracking system configured to capture image data of one or more of the mask and a face of the user, the tracking system further configured to track the fiducial marker, wherein the controller is configured to change the mask pose based at least in part on the image data, wherein the system is configured to automatically deliver the breathable gas to the user after detecting a state of the user, wherein the state of the user comprises a requisite sleep state of the user, wherein the requisite sleep state is one or more of predetermined by the user and is determined by the system, wherein the system delivers the breathable gas to the user after fulfillment of a time-based condition, wherein the system delivers the breathable gas to the user after one or more of passage of a predetermined amount of time and after a predetermined time of day is reached, wherein the robot comprises the tracking system, wherein the tracking system is configured to identify a face feature point, wherein the system moves the arm so as to bring the mask into contact with the face of the user after the face feature point is identified, wherein following bringing the mask into contact with the face of the user, the system commands the arm to maintain both an appropriate contact force with respect to the user's face and an appropriate position with respect to the user's face.

18. The system of claim 16, wherein following movement of the face of the user, the arm is configured to do one or more of move its location and change the contact force to maintain one or more of an appropriate contact force against the user's face and an appropriate position with respect to the user's face.

19. The system of claim 16, wherein following movement of the face of the user, the arm is configured to do one or more of move its location and change the contact force to maintain both an appropriate contact force against the user's face and an appropriate position with respect to the user's face.

20. The system of claim 16, wherein following a failure of the system to maintain both an appropriate contact force and an appropriate position, the system is configured to retract the arm so as to move the mask away from the face of the user.

21. The system of claim 20, wherein the system is configured, following retraction of the arm, to go into a mode in which the system awaits entry by the user into a requisite sleep state.

22. The system of claim 21, wherein upon entry by the user into the requisite sleep state, the system moves the arm toward the face of the user.

23. The system of claim 16, wherein the appropriate contact force and the appropriate position create a contact engagement between the mask and the face of the user.

24. The system of claim 16, wherein the controller is configured to change the pose of the mask based on one or more of the image data, lapse of a predetermined period of time, and an estimated sleep state of the user.

25. The system of claim 24, wherein the predetermined period of time represents an indication by the user to the system that the user is going to sleep after the predetermined period of time.

26. The system of claim 25, wherein the system places the mask on the face of the user after the predetermined period of time has lapsed.

27. The system of claim 24, wherein the estimated sleep state comprises one or more of a requisite sleep state and an estimation of stability of the user's sleep state.

28. The system of claim 27, wherein the system transitions from the sleep state to an approach state if the system determines that the estimated sleep state of the user is the requisite sleep state and if the system further determines that the estimated sleep state of the user is stable.

29. The system of claim 27, wherein the system transitions from the sleep state to a wait for sleep state in which the system waits if the system determines one or more of that the estimated sleep state of the user is not the requisite sleep state and that the estimated sleep state of the user is not stable.

30. A robotic ventilation system for correct mask placement comprising a fiducial marker, comprising:

a robot comprising an arm, the arm comprising a flange, the flange coupled to an end of the arm the arm configured to move the flange along a degree of freedom;

a mask coupled to the flange, the mask configured to deliver gas to a user, the mask comprising the fiducial marker;

a ventilator coupled to the mask, the ventilator configured to deliver the gas to the mask;

a gas tube coupled to both the mask and the ventilator, the gas tube configured to carry the gas between the ventilator and the mask;

a controller configured to change a pose of the mask, the controller further configured to control the delivery of the gas from the ventilator to the user; and a tracking system, the tracking system configured to capture image data of one or more of the mask and a face of the user, the tracking system further configured to track the fiducial marker, wherein the controller is configured to change the mask pose based at least in part on the image data, wherein the controller commands the arm to maintain one or more of an appropriate contact force with respect to the user's face and an appropriate position with respect to the user's face.

* * * * *